(12) United States Patent
Class et al.

(10) Patent No.: US 8,444,837 B2
(45) Date of Patent: May 21, 2013

(54) ARRANGEMENT FOR PRODUCING FLUID FLOWS AND/OR PARTICLE FLOWS, AND A METHOD FOR THE MANUFACTURE AND OPERATION THEREOF

(75) Inventors: Andreas Class, Linkenheim-Hochstetten (DE); Dominik Barz, Mannheim (DE)

(73) Assignee: Forschungszentrum Karlsruhe GmbH, Karlsruhe (DE)

(*) Notice: Subject to any disclaimer, the term of this patent is extended or adjusted under 35 U.S.C. 154(b) by 1180 days.

(21) Appl. No.: 12/278,254

(22) PCT Filed: Jan. 27, 2007

(86) PCT No.: PCT/EP2007/000715
§ 371 (c)(1),
(2), (4) Date: Aug. 4, 2008

(87) PCT Pub. No.: WO2007/090531
PCT Pub. Date: Aug. 16, 2007

(65) Prior Publication Data
US 2009/0008255 A1 Jan. 8, 2009

(30) Foreign Application Priority Data
Feb. 3, 2006 (DE) .................... 10 2006 004 887

(51) Int. Cl.
*B03C 5/02* (2006.01)
(52) U.S. Cl.
USPC ............ 204/547; 204/549; 204/643; 204/645
(58) Field of Classification Search
USPC ............. 204/450–454, 547, 549, 600–602, 204/643–645
See application file for complete search history.

(56) References Cited

U.S. PATENT DOCUMENTS
7,087,181 B2 8/2006 Schmidt et al.
2002/0195342 A1* 12/2002 Lee et al. ................. 204/451
(Continued)

FOREIGN PATENT DOCUMENTS
DE 10103399 8/2002
DE 10218325 11/2003
(Continued)

OTHER PUBLICATIONS

Ajdari A. "Electro-osmosis on inhomogeneously charged surfaces" Physical Review Letters USA, vol. 75, No. 4, Jul. 24, 1995, pp. 755-758, XP002429618, ISSN: 0031-9007, p. 757.
(Continued)

*Primary Examiner* — Keith Hendricks
*Assistant Examiner* — Bach Dinh
(74) *Attorney, Agent, or Firm* — Leydig, Voit & Mayer, Ltd.

(57) ABSTRACT

A device for producing at least one of fluid flows and particles flows includes a substrate having a substrate surface. The substrate surface includes a matrix including a plurality of regions having at least one of a different magnitude of a surface charge, a different sign of the surface charge, and a different height above the substrate. A fluid including at least partially electrically charged particles is disposed at the substrate surface. A first control element is configured to supply a plurality of electrical voltages to a plurality of electrode pairs. The electric field exerts a first force on a component of the fluid within an electrical double layer. The component is disposed adjacent to the substrate surface. The electric field exerts a second force within the double layer and outside the double layer, the second force is exerted on the at least partially electrically charged particles.

19 Claims, 16 Drawing Sheets

U.S. PATENT DOCUMENTS

| | | | |
|---|---|---|---|
| 2003/0143081 | A1 | 7/2003 | Rakestraw et al. |
| 2005/0230080 | A1 | 10/2005 | Paul et al. |
| 2008/0000772 | A1* | 1/2008 | Bazant et al. ............... 204/450 |

FOREIGN PATENT DOCUMENTS

| | | |
|---|---|---|
| DE | 60105979 | 9/2004 |
| EP | 595290 | 5/1994 |
| EP | 727661 | 8/1996 |
| EP | 1227060 | 7/2002 |
| EP | 1362827 | 11/2003 |
| WO | 9917883 | 4/1999 |

OTHER PUBLICATIONS

Stroock A. et al, "Patterning electro-osmotic flow with patterned surface charge", Physical Review Letters APS USA, vol. 84, No. 15, Apr. 10, 2000, pp. 3314-3317, XP002429619, ISSN: 0031-9007, p. 3317.

Barz D. et al., Model and verification of electrokinetic flow and transport in a micro electrophoresis device, Lab on a chip 2005, vol. 5, pp. 949-958.

Kirby B. et al., Zeta potential of microfluidic substrates: 2.Data for polymers, Electrophoresis 2004, vol. 25, pp. 203-213.

Petersen, N. et al., Effect of Joule heating on efficiency and performance for microchip-based and capillary-based electrophoretic separations: A closer look, Electrophoresis 2004, vol. 25, pp. 253-269.

Schasfort R., Field-Effect Flow Control for Microfabricated Fluidic Networks, Science 1999, vol. 286, pp. 942-945.

Chien R. et al., "Electroosmotic pumping in microchips with nonhomogeneous distribution of electrolytes" Electrophoresis 2002, vol. 23, pp. 1862-1869.

Takamura Y et al., Low-voltage electroosmosis pump for stand-alone microfluidics devices, Electrophoresis 2003, vol. 24, pp. 185-192.

Gitlin I. et al., Pumping based on Transverse Electrokinetic Effects, Applied Physics Letters 2003, pp. 1486-1488.

Studer V. et al., An integrate AC electrokinetic pump in a microfluidic loop for fast and tunable flow control, Analyst 2004, vol. 129, pp. 944-949.

Ramos A. et al.,"Electric Field-Induced Fluid Flow in Microelectrodes", J. Colloid and Surface Sciences 1999, vol. 217, pp. 420-422.

Ramos, A. et al., "Pumping of Liquids With Travelling-Wave Electroosmosis", Journal of Applied Physics 2005, vol. 97, pp. 084906-1 to 084906-8.

* cited by examiner

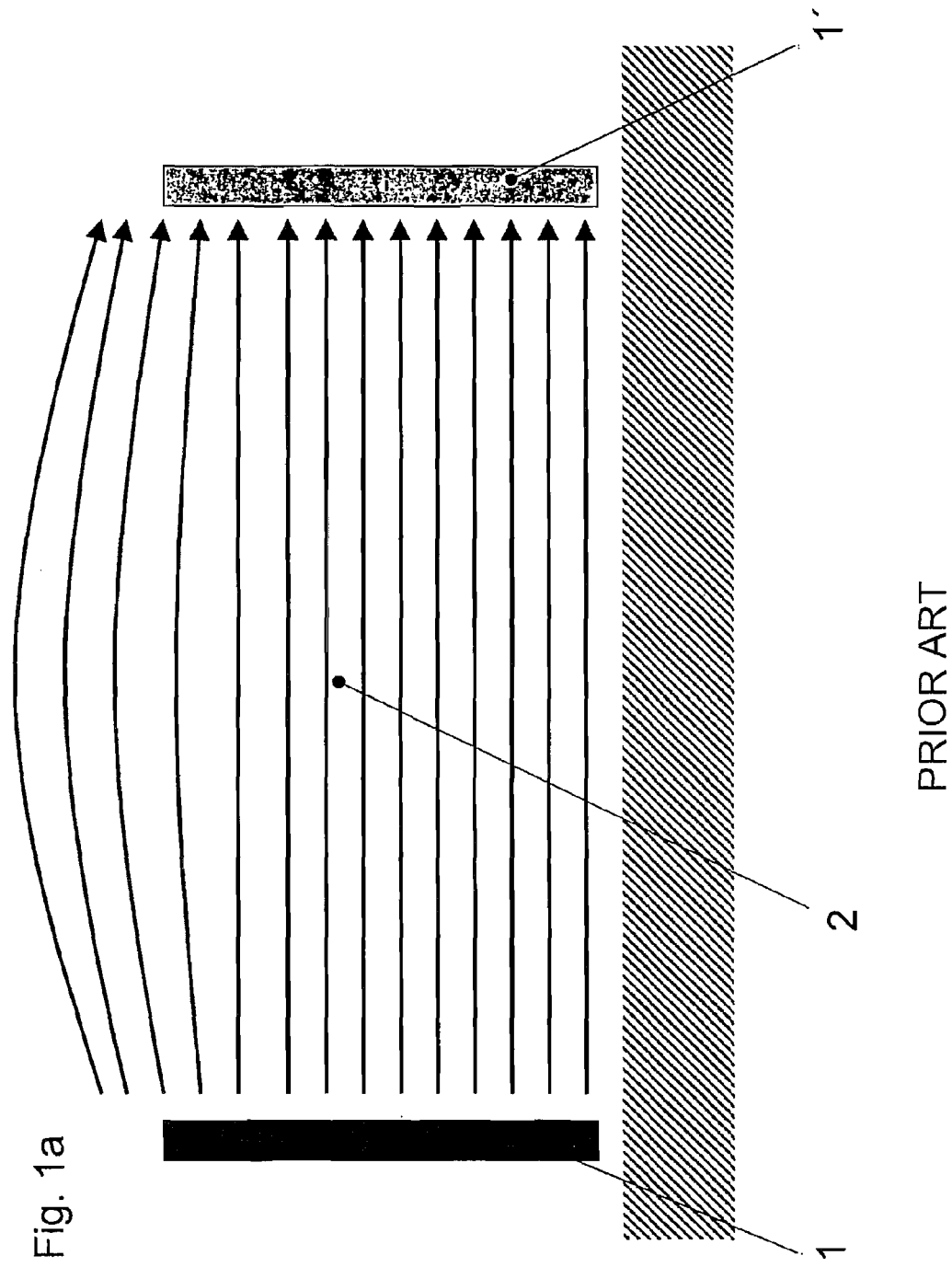

ARRANGEMENT FOR PRODUCING FLUID FLOWS AND/OR PARTICLE FLOWS, AND A METHOD FOR THE MANUFACTURE AND OPERATION THEREOF

CROSS REFERENCE TO PRIOR APPLICATIONS

This application is a U.S. National Phase application under 35 U.S.C. §371 of International Application No. PCT/EP2007/000715, filed on Jan. 27, 2007, and claims benefit to German Patent Application No. DE 10 2006 004 887.3, filed on Feb. 3, 2006. The International Application was published in German on Aug. 16, 2007 as WO 2007/090531 under PCT Article 21 (2).

FIELD

The present invention relates to an arrangement for producing fluid flows and/or particle flows of at least partially electrically charged particles contained in a fluid, respectively, to a method for manufacturing and for operating arrangements in accordance with the present invention, and to the use thereof as a freely programmable microfluidic analysis and/or synthesis unit or for locally cooling an adjacent microelectronic component or processor.

BACKGROUND

Fluid flows and particle flows of at least partially electrically charged particles can be realized by the application of electric fields. In this connection, electroosmosis and electrophoresis, which are classified as electrokinetic effects, are the important physical phenomena that occur.

Electroosmosis is described as the motion of a fluid under the influence of an externally induced electric field. At the surface (wall) of a substrate, electric charges are typically present. If the surface comes in contact with a fluid containing mobile electric charges, what is commonly known as an electrical double layer forms. The charge at the surface of the substrate attracts charge carriers of the fluid whose charge is opposite that of the surface charge. Because of the excess of charge, the electroneutrality of the fluid is then no longer given in the electrical double layer. The externally induced electric field causes the excess charge carriers in the electrical double layer to migrate in a preferential direction. The ensuing viscous interactions thereby induce a motion in the surrounding fluid. The velocity of the motion is proportional to the magnitude of the electric field. The proportionality factor is referred to as electroosmotic mobility.

Electrophoresis is understood to be the directed movement of at least partially electrically charged particles in a fluid or a gel under the action of an external electric field. The velocity of the particles is proportional to the magnitude of the electric field. The proportionality factor is referred to as electrophoretic mobility. Typically, the mobilities are specific and dependent on the surrounding fluid.

To drive a fluid flow by electroosmosis, an electric DC-voltage field is used that is generated by introducing an electrode pair into the fluid. The electric field component, which is tangential to the wall of a substrate, induces the flow in the region of the electrical double layer. Flow velocities in the mm/s range are typically attainable when electric fields on the order of kV/cm are used. The electroosmotic mobility depends, in particular, on the wall charge and the concentration of the mobile charge carriers in the fluid.

In response to a rise in the concentration of the mobile charge carriers, the number of particles upon which the electric field forces act increases, thereby inducing the flow. At the same time, however, the thickness of the electrical double layer decreases, thereby reducing the volume within which the forces act. These opposite effects yield an optimum charge concentration.

Due to the electroosmosis, it is possible for a flow to be produced without the use of mechanical components. Therefore, the principle is especially applicable to geometries having microscale dimensions. In a straight microchannel, a virtually uniform (plug-shaped) velocity profile is obtained over the width of the channel. This is especially beneficial for the transport of biological cells and other particles which must not be subject to the action of substantial shear forces.

Electrophoresis is used as a separation process for mixtures of at least partially electrically charged particles. To that end, the particles are typically injected into a microfluidic channel geometry having small dimensions, such as a capillary tube. The geometry is filled with a fluid which is used as a sample carrier. Similarly to the case of electroosmosis, an electrode pair is introduced into the geometry, and a DC-voltage field is produced. The particles move within the electric field in their specific direction of motion and at their specific velocity. If there is an appreciable difference in the electrophoretic mobility of the particle types, then a separation resolution of the particles by type is achieved. Migration velocities in the mm/s range are typically attainable when electric fields on the order of kV/cm are used.

In the context of both electrokinetic effects, an electrode pair is introduced into a fluid. For technical applications, the electric voltages are in the kV range. Since, typically, the fluids used are mostly composed of water, the high voltages induce electrolysis reactions, whereby the water breaks down into hydrogen and oxygen. These outgas therefore, induce undesired secondary flows and interfere with the local conductivity. Typical values of the equilibrium potentials of the decomposition reactions under standard conditions (activity 1 mole/dm$^3$, T=298 K) are on the order of 1 V. However, the equilibrium potential represents only the value required for the thermodynamic course of the reaction. In practice, due to reaction inhibitions, the value of the potential is appreciably higher than the equilibrium potential.

The high voltages used produce a relatively high electric current in the fluid, whereby the Joulean heat causes the fluid to be heated. The rise in temperature has a negative effect, especially in the case of analytical procedures. Natural convection and an inhomogeneous temperature profile degrade the separation efficiency and resolution. Therefore, the use of high voltages is frequently ruled out, and electroosmosis and electrophoresis are restricted in their technical use.

In *Model and Verification of Electrokinetic Flow and Transport in a Micro Electrophoresis Device, Lab on a Chip* 2005, volume 5, pp. 949-958, D. P. J. Barz and P. Ehrhard describe the theory of electroosmosis and electrophoresis. For straight and slightly curved geometries, the electroosmotic velocity $u_{EO}$ at the transition of the electrical double layer to the electrically neutral turbulent core, thus at a small distance to the wall, is expressed as $$u_{EO} = (q_{zeta} \cdot l_D / \eta) E_t,$$

$E_t$ being the external electric field component that is tangential to the wall. Prefactor $q_{zeta} \cdot l_D / \eta$ represents a formulation of the electroosmotic mobility, which is made up of the electric charge density $q_{zeta}$ at the shear plane between the adsorbed and diffuse charge layer, of the thickness $l_D$ of the electrical double layer, and of dynamic viscosity $\eta$ of the fluid. Given knowledge of zeta potential ζ, the charge density at the shear plane may be determined from $$q_{zeta} = -\epsilon \zeta / l_D,$$

$\epsilon$ being the permittivity of the fluid. The electrophoretic velocity $u_{EP}$ of an electrically charged particle under the influence of an electric field E is expressed as $$u_{EP} = \lambda_{EP} E.$$

The electrophoretic mobility $\lambda_{EP}$ of the particle can be calculated in the context of simple ions in infinite dilution, otherwise it can be determined by measurement.

In *Effect of Joule Heating on Efficiency and Performance for Microchip-Based and Capillary-Based Electrophoretic Separations: A Closer Look*, Electrophoresis 2004, volume 25, pp. 253-269, N. J. Petersen, R. P. H. Nikolajsen, K. B. Mogensen and J. P. Kutter illuminate how a temperature increase caused by Joulean heat influences electrophoretic separation systems. It is ascertained that the temperature of the fluid rises proportionally to the square of the electric field strength. In conventional capillaries, a boiling of the fluid can be observed already at relatively low electric field strengths. Such effects are not observed in planar microfluidic units given comparable conditions. Theoretical calculations reveal, however, that, in the case of capillaries and planar units, at or above a specific electric field strength, a radial temperature profile develops, and the separation efficiency is thereby degraded.

In *Zeta Potential of Microfluidic Substrates: 2. Data for Polymers*, Electrophoresis 2004, volume 25, pp. 203-213, and in *Zeta Potential of Microfluidic Substrates: 2. Data for Polymers*, Electrophoresis 2004, volume 25, pp. 203-213, B. J. Kirby and E. F. Hasselbrink Jr. describe the correlation between the Zeta potential and systems frequently used in microfluidics, thus the pairing of the fluid and substrate of the microfluidic unit. The zeta potential for glass, silicates and many plastics is predominantly negative over a broad variation range of the pH value and the fluid. However, plastics also exist, such as polyamides at pH≦6, that exhibit a positive zeta potential.

In *Field-Effect Flow Control for Microfabricated Fluidic Networks*, Science 1999, volume 286, pp. 942-945, R. B. M. Schasfort, S. Schlautmanm, J. Hendrickse and A. van den Berg describe a method for manipulating the zeta potential at the walls of microchannels which are fabricated from a semiconductor material, and discuss the results of such experiments. To this end, they introduce two electrodes into a microchannel that is filled with a fluid. The voltage between the electrodes induces an electroosmotic flow. An additional electric field is then induced between a third electrode outside of the channel wall and the fluid, perpendicularly to the channel wall. The zeta potential and, thus, the electroosmotic flow are influenced by the potential at the third electrode. It is described how, in response to the third electrode changing from a positive potential to a negative value, the flow direction and, therefore, the plus/minus sign of the zeta potential also change.

In *Patterning Electro-osmotic Flow with Patterned Surface Charge*, Physical Review Letters 2000, volume 84, pp. 3314-3317, A. D. Stroock, M. Weck, D. T. Chiu, W. T. S. Huck, P. J. A. Kenis, R. F. Ismagilov and G. M. Whitesides describe the behavior of the electroosmotic flow in a channel having different surface charges. To that end, two opposite walls of a rectangular channel are provided with two different coatings. Following the coating process, both walls have a similar charge density amount, but differ in their sign. If an electric field is then applied along the channel wall, a linear flow profile results. Starting from a positive velocity u at the negatively charged wall, the velocity falls to zero when approaching the middle of the channel, to finally reach value −u at the positive wall. In another configuration, one channel wall is coated in a such a way that a regularly alternating structure of positive and negative surface charges results. In response to the application of an electric field in the direction of the channel, vortices form over the treated sections. The direction of rotation of the vortices is dependent on the sign of the surface charge. When such an arrangement is used, it is not possible for a fluid transport of any significance to be achieved. Moreover, such an arrangement cannot be used for analytical processes.

In *Electroosmotic Pumping in Microchips With Nonhomogeneous Distribution of Electrolytes*, Electrophoresis 2002, volume 23, pp. 1862-1869, R.-L. Chien and L. Bousse describe coating the interior of a capillary with a polymer in order to reduce the value of the zeta potential and thus the electroosmotic flow velocity.

In *Low-Voltage Electroosmosis Pump for Stand-Alone Microfluidics Devices*, Electrophoresis 2003, volume 24, pp. 185-192, Y. Takamura, H. Onoda, H. Inokuchi, S. Adachi, A. Oki and Y. Horiike describe a pump based on fluid flows produced by electroosmosis. To increase their efficiency, it is theoretically proposed to connect in series two individual pumps having opposite zeta potential, which, from opposite electric fields, produce the same flow direction. However, the authors reject this approach as being hardly feasible. Rather, they construct a highly efficient pump by connecting in series regions of small and large cross section that are inserted in a meander form between a positive and a negative electrode. It turns out that this configuration has the drawback of a large surface-area requirement and low flexibility.

The European Patent EP 0 727 661 B1 describes a method and a device for mixing fluids, which provide for an electroosmotic pump to transport the two fluids to be mixed to a connection point, where they are mixed. The inherent disadvantages here are the use of capillaries, the high voltage requirement, as well as the lack of flexibility.

In *Pumping Based on Transverse Electrokinetic Effects*, Applied Physics Letters 2003, volume 83, pp. 1486-1488, I. Gitlin, A. D. Stroock, G. M. Whitesides and A. Ajdari describe a microfluidic pump where a transversal electric field induces a longitudinal flow along the channel direction in a channel into which oblique recesses have been introduced into one wall. This article also discusses controlling such flows by the application of voltages between channel intersections. In this arrangement, the flow is bound to the channels, the rate of net transport is low, and the essentially helical trajectories inevitably subject the fluid flows at the intersections to a mixing process that is not necessarily desirable.

From V. Studer, A. Pépin, Y. Chen and A. Ajdari, *An Integrated AC Electrokinetic Pump in a Microfluidic Loop for Fast and Tunable Flow Control*, Analyst 2004, volume 129, pp. 944-949, an asymmetrical electrode arrangement on a homogeneous substrate is described, which, by employing an AC voltage in the 1-10 kHz range, functions as a microfluidic pump. Other arrangements of this kind which are operated using AC voltage, are described in the European Patent Specification EP 0 595 290 B1 and the German Patent Application DE 101 03 399 A1. One possible mechanism of the alternating-field electroosmosis resides in the heating of the fluid by the induced electric field. In response to the heating, the permittivity of the fluid changes locally. Electric volumetric forces can thereby be induced in the presence of an inhomogeneous electric field. However, this phenomenon is typically not very pronounced.

In *AC Electric Field-Induced Fluid Flow in Microelectrodes*, J. Colloid and Surface Sciences 1999, volume 217, pp. 420-422, A. Ramos, H. Morgan, N. G. Green and A. Castellanos describe a different thesis. In the case of alternating-field electroosmosis, not only is the electric field inhomogeneous and dependent on the frequency, but a component of the electric charge density of the electrode surface is coupled to the frequency. At high frequencies, the potential mostly falls off in the electrolyte, the induced charge in the electrical double layer is small, and the resulting flow, therefore, as well. At low frequencies, the potential mostly falls off over the electrical double layer, the tangential component of the electric field is small, and, again, no appreciable flow develops. However, an appreciable laminar flow forms at middle frequencies.

In *Pumping of Liquids With Travelling-Wave Electroosmosis*, Journal of Applied Physics 2005, volume 97, pp. 084906-1 to 084906-8, A. Ramos, H. Morgan, N. G. Green, A. Gonzales and A. Castellanos describe another arrangement for generating an electroosmotic flow. To that end, an arrangement of a plurality of regularly interspaced, small symmetrical electrodes are attached to the channel wall. A voltage signal in the form of a sinusoidal signal is then induced at the electrode arrangement. The voltage at two successive electrodes exhibits a 90° phase displacement. This arrangement makes it possible for appreciable liquid flows to be produced at amplitudes of 1 volt. However, the prevailing mechanisms are not fully clarified. Thus, for example, above a certain threshold value of the voltage amplitude, the flow direction changes. Moreover, the threshold value appears to be dependent on the electrode material. Furthermore, a relatively high velocity of the fluid tangentially to the main flow direction is apparent in this method, which can be problematic in terms of an analytical use.

European Patent Application EP 1 362 827 A1 describes the principle of producing fluid flows and/or particle flows of at least partially electrically charged particles contained in a fluid, where the force derived from oppositely directed electric fields induces a rectified flow of the fluid tangentially to the surface of the substrate.

A method known from the prior art for utilizing electrokinetic effects for lab-on-a-chip applications is depicted in FIG. 1a and FIG. 1b. Two electrodes are interspaced at a considerable distance in a microstructure. In accordance with FIG. 1a, a high voltage is applied in between the two electrodes to generate an electric field that penetrates a large volume of the microstructure in such a way that a current flow and, thus, Joulean heat is induced everywhere in this region.

Due to the relatively uniform zeta potential along the surface of the substrate in accordance with FIG. 1b, the electric field generates a uniform force field and, therefore, an electroosmotic flow. A mixture of at least partially electrically charged particles within the electrical double layer and externally therefrom resolves into its constituents under the influence of the electric field.

In terms of the application in an electrophoretic separating unit, this is a desired effect. However, the arrangement does not permit the simple transport of mixtures of at least partially electrically charged particles, which, in many cases, has a disadvantageous effect. Moreover, due to the high voltage between the electrodes, there is still the probability of electrolytic decomposition reactions of the fluid.

FIGS. 1a and 1b illustrate the prior art. If two adjacent electrodes 1, 1' are supplied with a positive and negative DC voltage, respectively, this yields an electric field 2. If a homogeneous surface charge is present at surface 3, a force field 4 forms within the electrical double layer, inducing a flow 5. Positively charged particles migrate in direction 6 of the negatively charged electrode. Negatively charged particles migrate in direction 7 of the positively charged electrode.

SUMMARY

An aspect of the present invention is to provide an arrangement for producing fluid flows and/or particle flows of at least partially electrically charged particles contained in a liquid, that will address the aforementioned limitations. In particular, that such an arrangement be able to provide a spatially extensive net transport of the fluid and/or of particles contained in the fluid, that may be largely freely controlled by external means.

In an embodiment, the present invention provides a device for producing at least one of fluid flows and particles flows is provided in the present invention. The device includes a substrate having a substrate surface. The substrate surface includes a matrix including a plurality of regions having at least one of a different magnitude of a surface charge, a different sign of the surface charge, and a different height above the substrate. A fluid is disposed at the substrate surface and includes at least partially electrically charged particles. A plurality of electrode pairs are disposed on the substrate surface. A first control element is configured to supply a plurality of electrical voltages to the plurality of electrode pairs so as to generate, by each of the plurality of electrode pairs, an electric field in response thereto. The electric field exerts a first force on a component of the fluid within an electrical double layer, the component being disposed adjacent to the substrate surface. The electric field exerts a second force within the double layer and outside of the double layer. The second force is exerted on the at least partially electrically charged particles.

BRIEF DESCRIPTION OF THE DRAWINGS

The present invention is explained in greater detail in the following with reference to exemplary embodiments and the figures. Specifically, the figures show:

FIG. 1a an electric field between two electrodes introduced into a fluid (prior art);

FIG. 2b a fluid flow in the context of an electrical double layer along the surface of the substrate having regions of homogeneous surface charge in an electric field in accordance with FIG. 2a;

FIG. 2c a fluid flow in the context of an electrical double layer and the electrophoretic transport of at least partially electrically charged particles along the surface of a substrate having regions of alternating wall charge in an electric field in accordance with FIG. 2a;

FIG. 2d a fluid flow and electrophoretic transport of at least partially electrically charged particles, in the context of an electrical double layer, along a surface of a substrate having regions of different surface charge in an electric field in accordance with FIG. 2a;

DETAILED DESCRIPTION

Figure 1B:
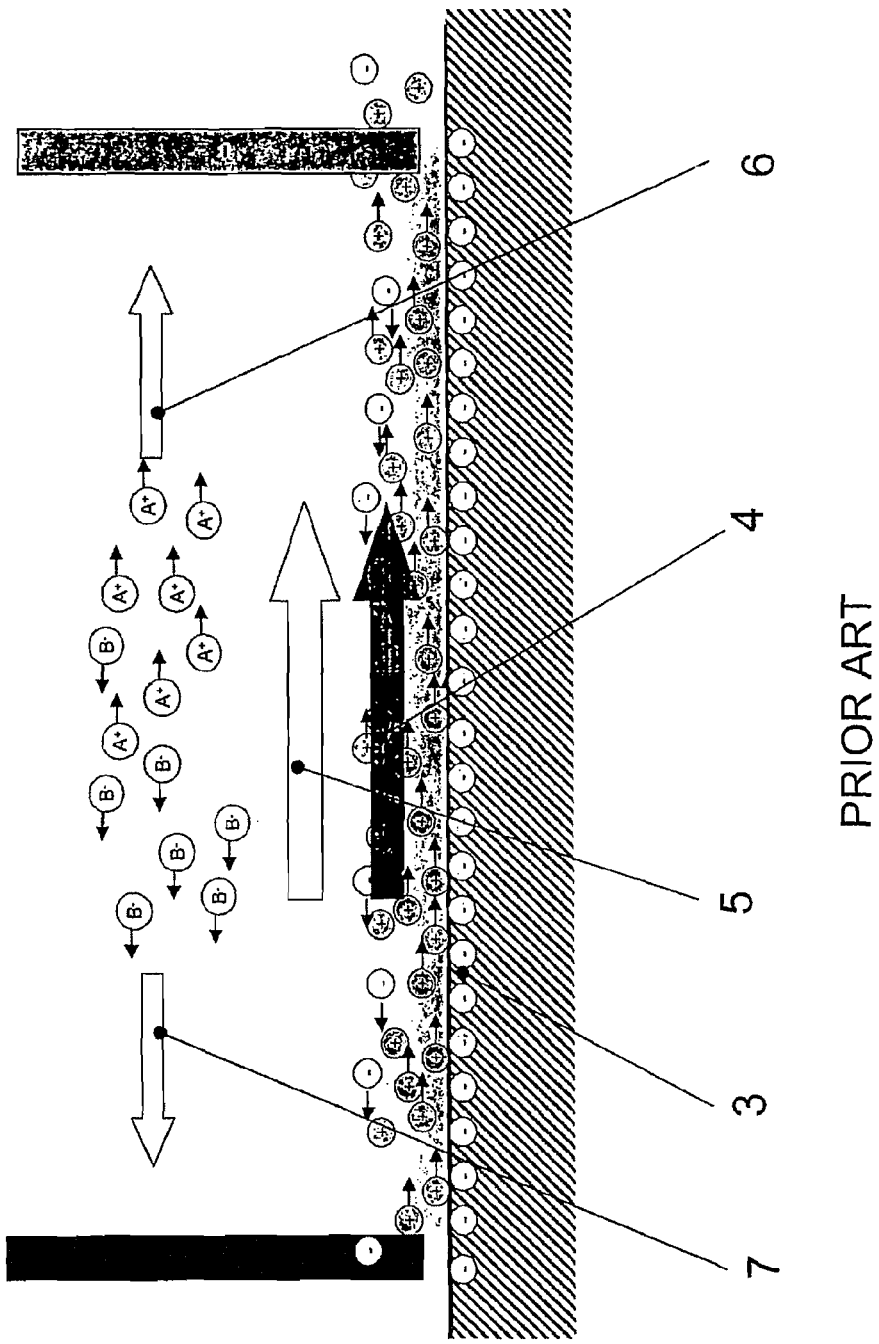
FIG. 1b a fluid flow in the context of the presence of an electrical double layer and the electrophoretic separation of a mixture of at least partially electrically charged particles in an electric field in accordance with FIG. 1a (prior art)

Besides the fluid and/or particle transport, it is intended that an arrangement according to the present invention be able to provide at least two other basic functions of a "lab on a chip", such as focusing and preconcentration, flow mixing, flow distribution, flow bifurcation and flow intersection, metering, tagging, reaction and analysis or detection.

It is also an aspect of the present invention to provide a method for manufacturing an arrangement of this kind, as well as for the operation and use thereof.

An arrangement according to the present invention includes a substrate of a non-conductor or of a semiconductor, such as glass, plastic or silicon, for example, as well as controllable means for supplying electric voltages for a multiplicity of electrode pairs, which are applied to the substrate in the form of a matrix, i.e., a two-dimensional array, preferably in a checkered pattern. When a voltage is applied, an electric field is hereby generated between the electrode pairs in question, that, within an electrical double layer, exerts a force on a fluid adjacent to the substrate, and, as the case may be, additionally or exclusively, both within the electrical double layer, or also externally therefore, exerts a force on the particles.

In this context, the surface of the substrate should be formed in a way that enables the force derived from oppositely directed electric fields to induce a rectified flow of the fluid tangentially to the surface of the substrate, and, as the case may be, additionally or exclusively, renders possible the electrophoretic mass transport within the electrical double layer, or also externally therefrom, likewise in a direction normal to the surface of the substrate.

The interelectrode distances are preferably at least as great as the thickness of the electrical double layer. By selecting small electrode distances of 10 nm to 1 mm, preferably of 100 nm to 100 µm, high electric field strengths are attainable, as desired, in response to the application of potentials having low absolute values.

Each electrode is preferably configured between two regions on the surface of the substrate that each have different surface properties. In one preferred embodiment, two adjacent regions on the surface of the substrate have the same dimensions and, therefore, the same interelectrode distances, and each have a positive and a negative wall charge. This statement is synonymous with the ascertainment that the zeta potential differs in its sign in two respective, adjacent substrate fields.

In one alternative embodiment, two adjacent regions on the surface of the substrate each have a different surface charge density amount, given the same sign. This statement is synonymous with the ascertainment that, in two respective, adjacent substrate fields, the zeta potential differs in its amount, but not in its sign. As the difference in the amount of the surface charge density, respectively in the amount of the zeta potential between two adjacent regions increases, the flow velocity increases.

In one preferred embodiment, at least the surface of the substrate is made of a semiconductor material, such as of a doped or undoped silicon wafer, for example. In accordance with this embodiment, the controllable means for supplying electric voltages for the multiplicity of electrode pairs, which are already applied to the substrate in the form of a matrix, are also advantageously used for influencing the surface charge, i.e., the zeta potential in regions on the surface of the substrate. It may also be alternatively provided for the surface charge to be influenced by a second controllable means that is separately mounted for this purpose. It is advantageous for the electrodes to be grouped in a checkered pattern and jointly switched.

One alternative embodiment provides for one of two adjacent regions on the surface of the substrate to be provided in each instance with a coating of two polymers having a different surface charge. The effective result is that the zeta potential differs in its sign in two respective, adjacent substrate fields.

In another embodiment, each electrode is configured between two regions on the surface of the substrate whose height above the substrate differs. This may be accomplished in that, in each case, one of the fields has a recess whose depth preferably corresponds at most to the interelectrode spacing in an electrode pair.

The present invention also relates to a device that is bounded by at least two arrangements according to the present invention, between which the fluid is located. The at least two arrangements according to the present invention are preferably disposed in mutual opposition.

The present invention also relates to a method for manufacturing an arrangement for producing liquid flows and/or particle flows of at least partially electrically charged particles contained in a liquid, encompassing the following steps.

First, a substrate is prepared, upon which controllable means for interconnecting the multiplicity of electrodes are placed. Subsequently thereto, the electrodes are surface-mounted on the substrate, and the substrate surface is treated, thereby providing each of two adjacent regions with different surface properties. Once a fluid is applied to the substrate, the arrangement according to the present invention is ready for use.

The substrate surface is structured to form individual regions in order to preferably galvanically isolate two mutually adjacent regions from one another. Each region is subsequently electrically contacted. The contacts are connected to the controllable means for supplying electric voltages, making it possible for the surface charge of the regions to be individually influenced. The electrodes are then preferably surface-mounted on the substrate at those locations situated between two regions. Once the electrodes have been contacted in pairs and these contacts have been connected to the controllable means for supplying electric voltages, a fluid is applied to the substrate.

An arrangement of this kind is able to be produced by coating a glass or plastic substrate only in specific regions with polycycloolefin or polyamide, whose zeta potentials, at a pH of, at most, 6, have a positive sign, or with a metal oxide having a positive surface charge, such as aluminum oxide, for example. The remaining regions on the substrate remain exposed, so that, there, the glass or the plastic, which have a negative zeta potential and thus a negative wall charge, form the surface of the substrate. The pH value may be adjusted using a buffer to which the fluid is added.

In one alternative approach, the surface is made of a semiconductor, is subdivided between the electrodes into galvanically isolated regions, and is electrically contacted. This makes it possible to adjust an individual potential in each region that is used to produce a desired surface charge or a desired zeta potential.

A multiplicity of electrodes are applied to the surface of the substrate at a small mutual distance. If an electric voltage is applied to an electrode pair, an electric field is then generated in between the electrode pair, thereby impelling the flow within the electrical double layer of the fluid adjacent to the surface of the substrate. In addition, an arrangement of this kind renders possible the electrophoretic particle transport within the electrical double layer and externally therefrom.

By introducing a multiplicity of electrodes in a matrix array, a local fluid flow and/or a local particle flow are produced. Producing a spatially extensive flow, respectively a spatially extensive particle flow, requires that the voltage increase from electrode to electrode, overall, therefore, it again being necessary for high voltages to be applied. However, the present invention provides that the surface of the substrate be formed in a way that yields a spatially extensive flow, respectively a spatially extensive particle flow, already at low AC voltages. In this context, spatially extensive means that a fluid flow, respectively a particle flow ensues that extends over distances that are substantially greater than the interelectrode spacing of adjacent electrodes.

Figure 2A:
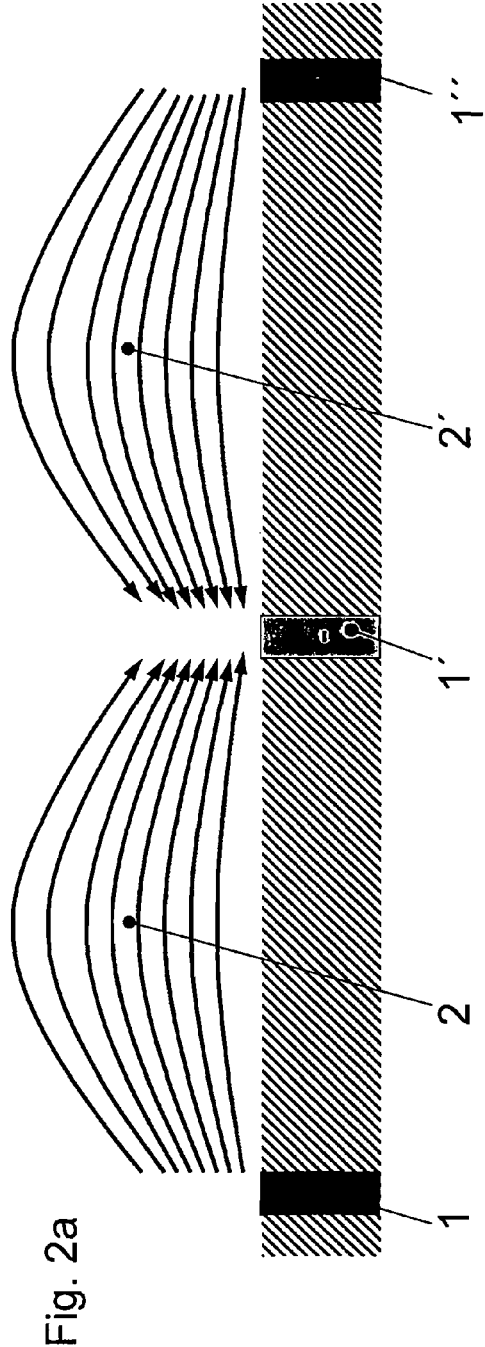
FIG. 2a electric fields between electrodes, which are surface-mounted on the substrate and whose DC voltages are configured to alternate with one another.

If two adjacent electrode pairs, which are applied to the surface of the substrate, are supplied with a positive, respectively a negative DC voltage, one obtains electric fields which alternate in their direction in accordance with FIG. 2a. When a suitable array is used, the electric fields penetrate a smaller volume than in the case of a comparable electric field that is generated by introducing a conventional electrode array. Therefore, given the same flow densities, less Joulean heat is produced in the design according to the present invention.

Figure 2B:
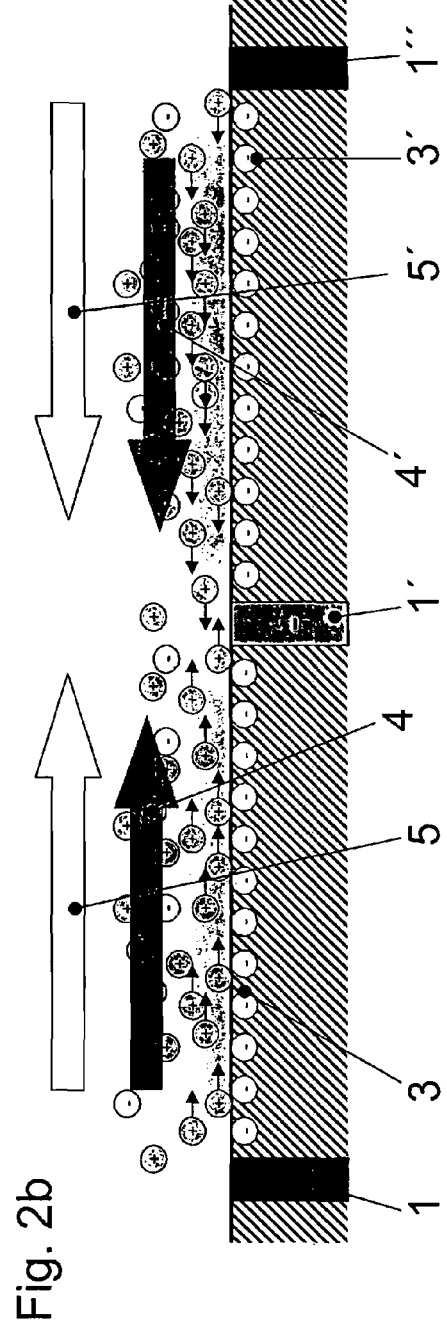

If the wall is made of a homogeneous material, an alternating force field is produced as illustrated in FIG. 2b. This only induces local flows having an alternating flow direction that do not result in a net flow along the surface of the substrate.

Figure 2C:
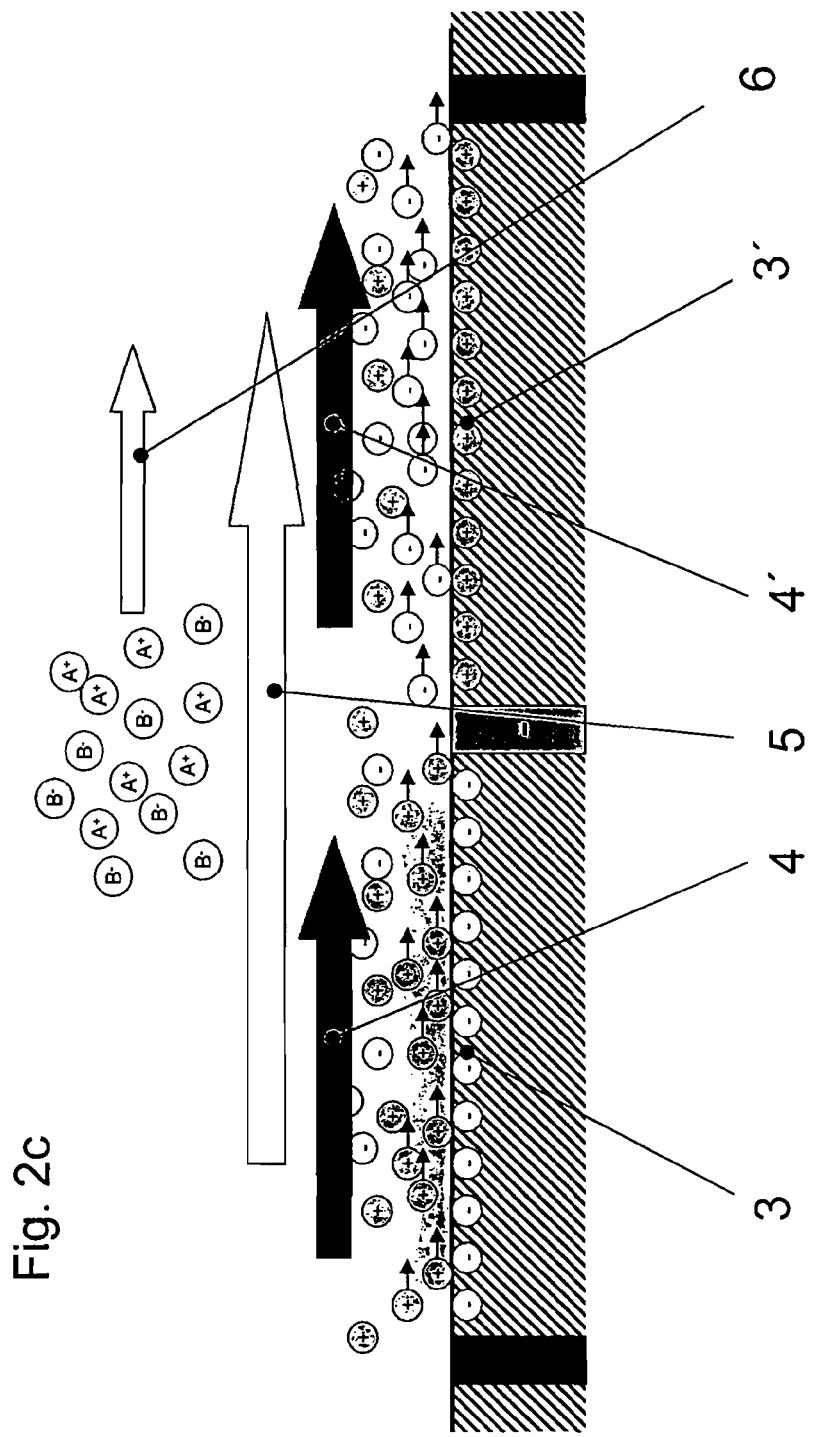

The principle of one preferred arrangement is schematically shown in FIG. 2c. In each case, alternating regions having a positive and negative surface charge are located between two electrodes. The result, accordingly, is an alternating excess of negative and, respectively, positive ions in the electrical double layer above the surface of the substrate. Together with the electric fields having alternating directions, a force effect is derived that is rectified along the entire surface and thus results in a net flow of the fluid.

If a mixture of at least partially electrically charged particles is contained within the electrical double layer, or externally therefrom, such particles are then able to be transported in the arrangement according to the present invention without being resolved in accordance with the species thereof. On the one hand, this is because the particles are located outside of the range of the electric field and only move then at electroosmotic velocity. On the other hand, a transport without separation effect also takes place under the influence of the electric field. The particles then move with the superposition of the electroosmotic velocity and their specific electrophoretic velocity. However, since the electric fields alternate, the direction of the electrophoretic velocity also alternates, so that, on the average, the separation effect is cancelled.

However, achieving a net flow does not absolutely entail alternating the wall charges so definitively. Even when the surface charges have the same sign everywhere, but the amount of the surface charge density differs, the result is a net flow in accordance with FIG. 2d, since the opposite flows, which occur in each case between two adjacent electrode pairs, do not fully compensate for each other. One possible electrophoretic transport of at least partially electrically charged particles also takes place in this arrangement along the lines of the comments regarding FIG. 2b.

Figure 3:
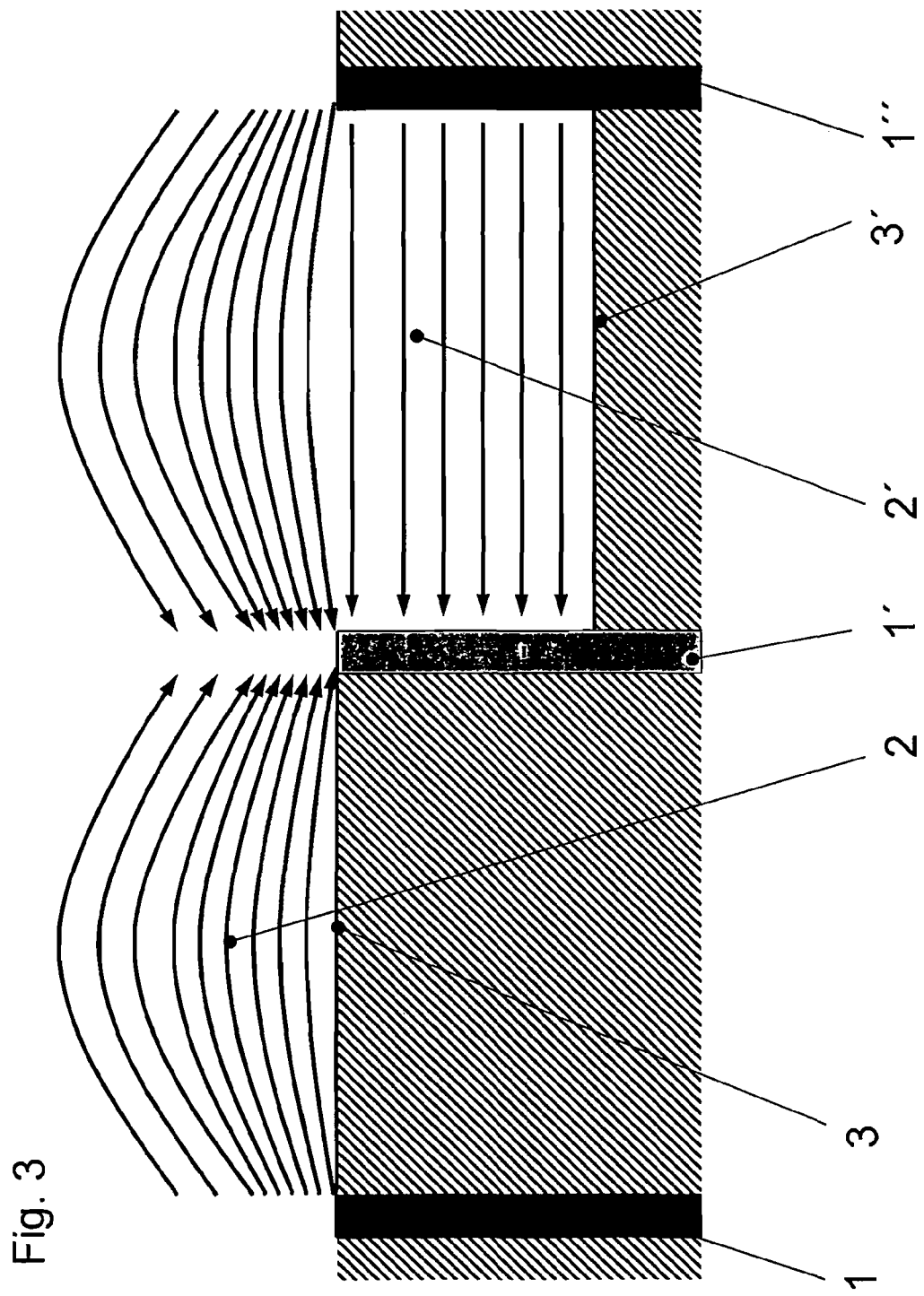
FIG. 3 electric fields in a channel between electrodes which are positioned in relation to each other between surfaces of alternating height and having alternating DC voltage.
Figure 4:
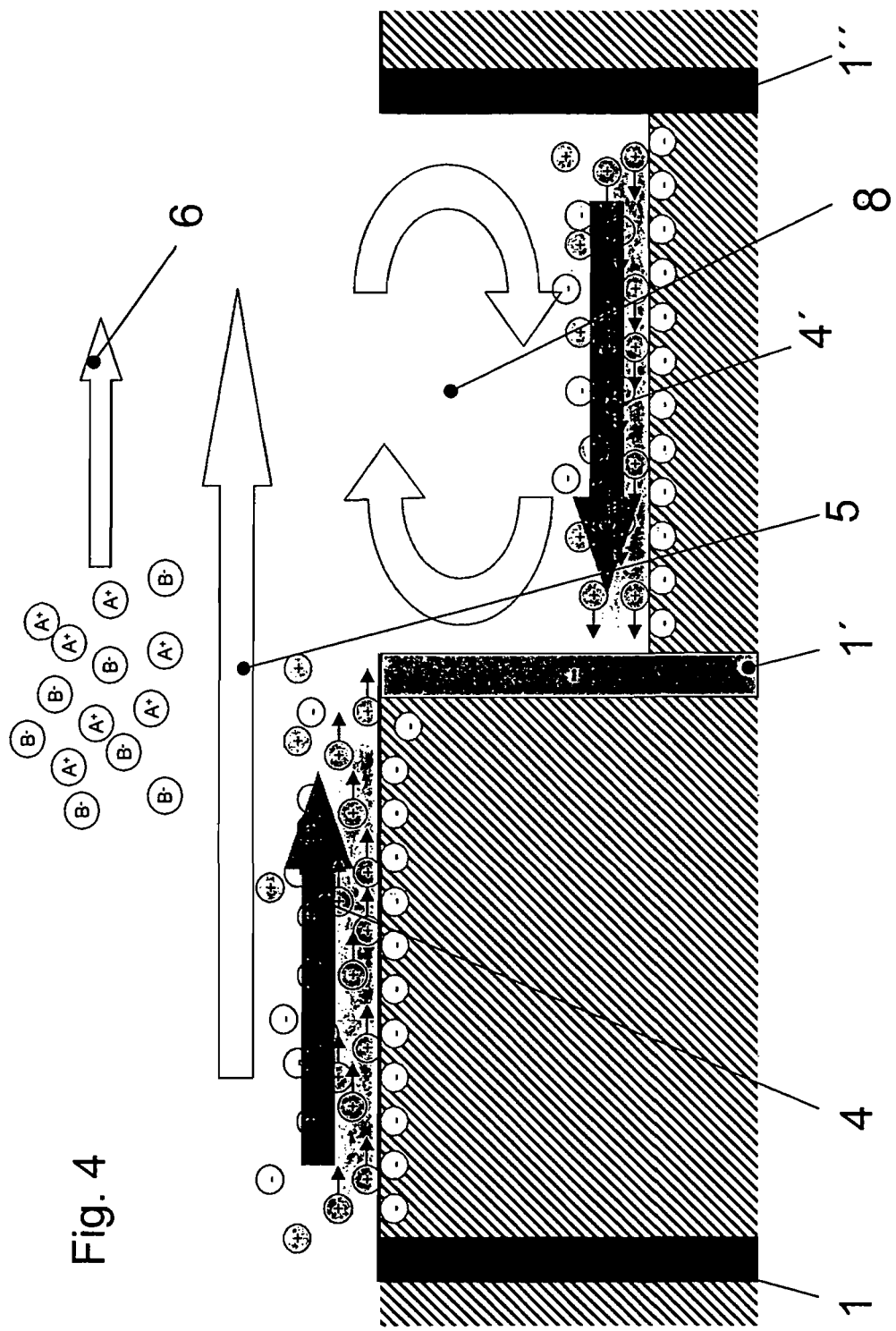
FIG. 4 a fluid flow in the context of an electrical double layer and the electrophoretic separation of at least partially electrically charged particles along substrate surfaces of alternating height in an electric field in accordance with FIG. 3.

Instead of selecting different materials in alternating succession for adjacent regions on the surface of the substrate, the surface may be provided with an alternating geometry in order to obtain a net flow and/or a desired electrophoretic particle flow. FIG. 3 and FIG. 4 show a variant where the surface is made of a homogeneous material. Alternatively, the surface in between an electrode pair is designed to be level, and, between electrode pairs adjacent thereto, a recess, whose depth corresponds to the interelectrode spacing in one electrode pair, is introduced into the surface. FIG. 3 shows schematically the electric fields that are obtained in an arrangement of this kind.

With regard to the flow impelling process, only that component of the electric field, which is tangential to the surface of the substrate, is determinative. For that reason, as illustrated in FIG. 4, a flow vortex forms in the recess which intensifies the net flow of the fluid tangentially to the surface. In such an arrangement, a mixture of at least partially charged particles is transported without electrophoretic separation.

Another advantageous embodiment presents itself when an arrangement of this kind has as its function, an electrophoretic separation of at least partially electrically charged particles. It suffices then to duplicate the arrangement from FIG. 3 on the opposite side as well, and to vary the interelectrode distances. The resulting electric fields of such an arrangement are shown schematically in FIG. 5. Between the upper and lower surfaces (walls), equidirectional, mutually superposed electric fields form. No electric field is present in the space outside of the recesses since the penetration depth of the electric fields is correlated with the interelectrode spacing. An electroosmotic flow, as illustrated in FIG. 6, results therefrom. Flow vortices, which intensify the flow along the walls, form in the recesses. A mixture of at least partially electrically charged particles is subjected to an electric field only via the walls; the successive fields are always equidirectional, thereby rendering possible an electrophoretic separation.

Furthermore, the present invention includes arrangements of electrodes and materials on the surface of the substrate, where the electroosmotic fluid flow driving, respectively the electrophoretic mass transport is used in addition to the fluid and/or particle transport in order to provide two further basic functions of a lab on a chip. The basic functions include, in particular, electrophoretic separation of at least partially electrically charged particles, focusing and preconcentration, flow mixing, flow distribution, flow bifurcation and flow intersection, metering, tagging, reaction and analysis or detection.

The present invention includes a freely programmable lab on a chip, which is composed of a matrix array of electroosmotic fluid flow drives, respectively of electrophoretic particle flow drives, which assume the function of impelling the entire fluid flow and/or particle flow on the chip, as well as of mixing the reagents, of analyzing the at least partially electrically charged particles, and of feeding samples to sensors.

The arrangement according to the present invention and the method for the operation thereof may be advantageously compared to a freely programmable electronic chip. The low-voltage electroosmotic drive, respectively electrophoretic drive, corresponds in function to transistors and printed conductors. However, the chip itself first realizes its full functionality in the electronic interconnections, the feeding and removal of fluids and/or of at least partially electrically charged particles, and in sensors mounted thereon.

Another use of the arrangement is locally cooling an adjacent microelectronic component or processor.

The method according to the present invention exhibits the following advantages:

The fluid drive by electroosmosis and the particle transport/separation by electrophoresis operate at low voltages.

In comparison to known methods, the generated electric fields occupy less space.

The lab on a chip has small dimensions.

The lab on a chip is able to be refined in such a way that it is freely programmable within a broad range and is thus flexible.

In FIG. 1 through 6, circles marked + represent positively charged ions and those marked −, negative ions in the electrical double layers, respectively at the surface (wall) of the substrate. On the other hand, circles marked A+ represent positive particles and circles marked B−, negatively charged particles within the electrical double layer, or externally therefrom.

FIG. 2a includes two electrode pairs 1, 1' and 1', 1" which are integrated in the wall. The electrode pairs are supplied with a positive and negative DC voltage, respectively, thereby yielding two alternating electric fields 2, 2'.

In FIG. 2b, surfaces 3, 3' between electrode pairs 1, 1' and 1', 1" have a homogeneous surface charge. Two alternating force fields 4, 4' form within the electrical double layer. They only induce local flows 5, 5' having an alternating direction that do not result in a net flow.

However, if, as illustrated in FIG. 2c, surfaces 3, 3' are provided with an alternating surface charge, then, together with alternating electric fields 2, 2', rectified force fields 4, 4' are obtained. A net flow 5 results therefrom. The electrically charged particles outside of the boundary layer move on average in the direction and at the velocity of net flow 6.

Figure 2D:
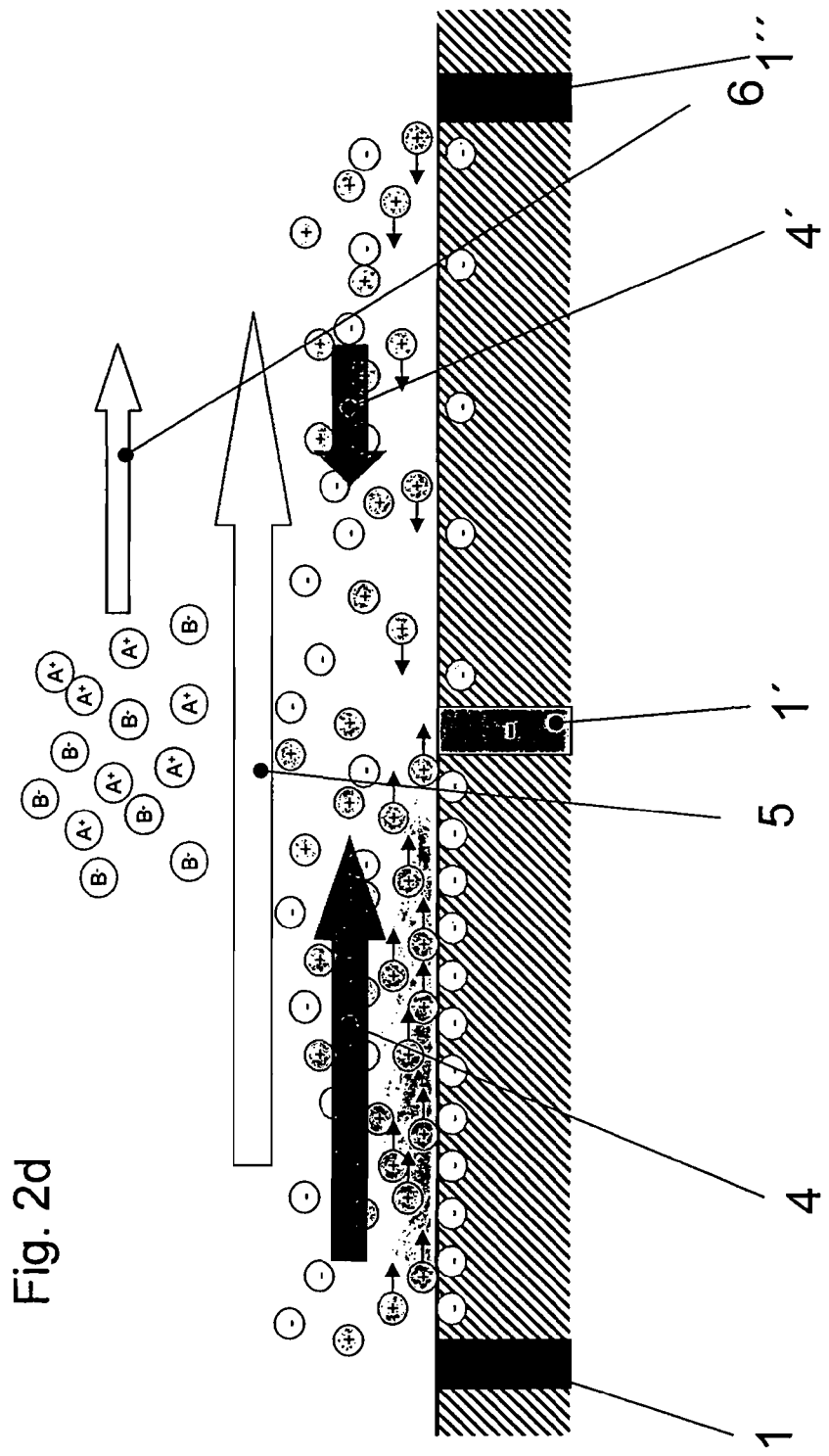

In FIG. 2d, the surface charges have the same sign everywhere, but the amount of the surface charge densities differs. A net flow 5 likewise results therefrom since alternating force fields 4, 4', which occur between two adjacent electrode pairs 1, 1' and 1', 1", respectively, do not fully compensate for each other. The electrically charged particles outside of the boundary layer move on average in the direction and at the velocity of net flow 6.

In FIG. 3, surfaces 3, 3', which have a homogeneous surface charge, are provided with an alternating geometry, thereby yielding electric fields 2, 2'. Alternatively, the surface in between electrode pair 1, 1' is designed to be level, and a recess is introduced into the surface in between electrode pair 1', 1" adjacent thereto.

Force fields 4, 4' generated thereby are shown in FIG. 4. A flow vortex 8, which intensifies net flow 5 of the fluid, forms in the recess. The electrically charged particles outside of the boundary layer pass through the alternating fields. Therefore, on average, they move in the direction and at the velocity of net flow 6.

Figure 5:
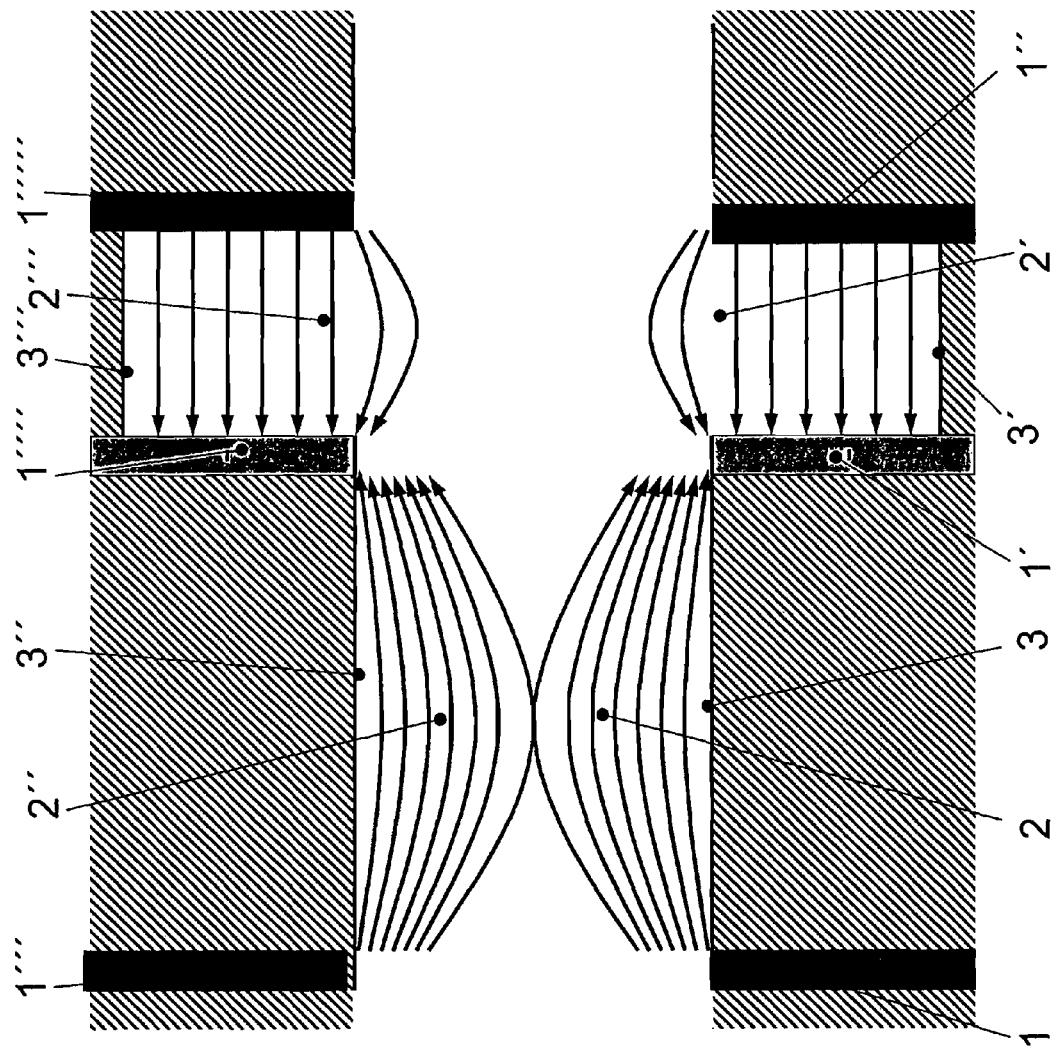
FIG. 5 electric fields between electrodes which are surface-mounted on the substrate and whose voltages are configured to alternate with one another. The electrode pairs are mounted on two opposing sides of a channel.
Figure 6:
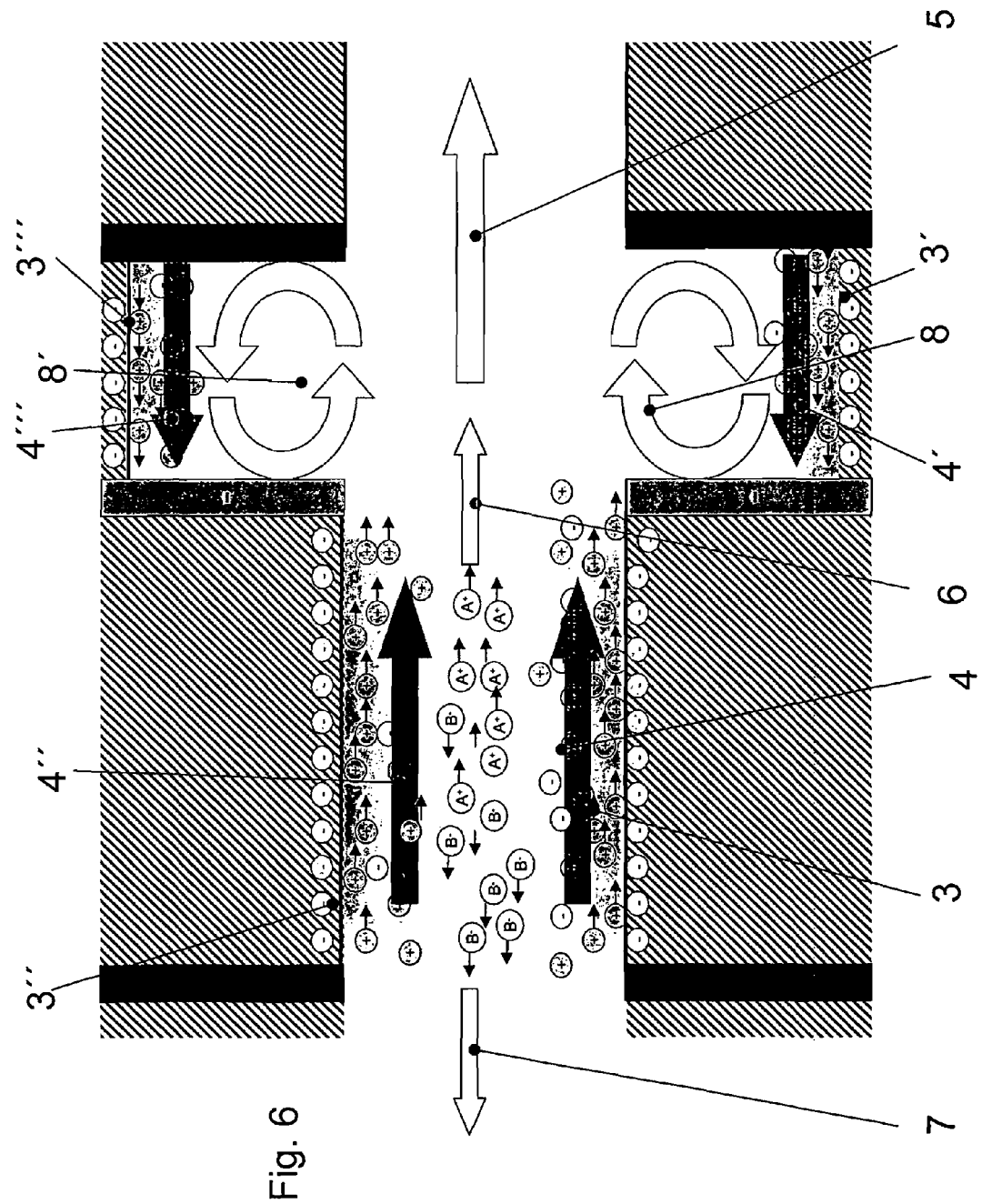
FIG. 6 a fluid flow in the context of an electrical double layer and the electrophoretic separation of at least partially electrically charged particles along surfaces of alternating height in an electric field in accordance with FIG. 5.

FIG. 5 shows an arrangement having two opposite sides which each have a surface according to the present invention exhibiting a horizontal symmetry. To that end, surfaces 3, 3', respectively 3", 3'" have an alternating design, so that a recess is thereby formed. Between electrode pairs 1, 1' and 1', 1", respectively 1"', 1"" and 1"", 1""', alternating DC voltages are applied, so that electric fields 2, 2', 2", 2'" result therefrom. Electric fields 2', 2'" hardly penetrate into the fluid since the interelectrode spacing between the electrodes in question is small.

FIG. 6 illustrates force fields 4, 4', 4", 4'" that form due to the homogeneous surface charge of walls 3, 3', 3", 3'". In the recesses, flow vortices 8, 8' form which intensify net flow 5. A mixture of at least partially electrically charged particles between walls 3, 3' and, respectively, 3", 3'" passes through electric fields only in one direction. Therefore, relative to the velocity of net flow 5, the particles move in direction 6 or in direction 7, depending on the charge.

Figure 7:
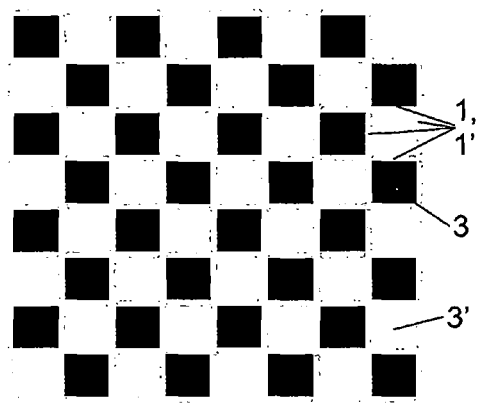
FIG. 7 a schematic design of a lab on a chip in a checkered configuration.

FIG. 7 shows schematically the design of a lab on a chip in a checkered configuration. To this end, the surface is patterned into square regions 3, 3', regions 3 having a positive surface charge and regions 3' having a negative surface charge alternating with one another. Each individual region 3, 3' is surrounded by four individual electrodes 1, 1', 1", 1'" which are individually addressable. The form is disposed in plane symmetry, for example, in the base and cover of the lab on a chip.

The flow direction, respectively the electrophoretic particle flow direction, is symbolically explained in the following examples by the indication of cardinal directions, north of a flow, respectively of a particle flow, corresponding to upwards.

Figure 8A:
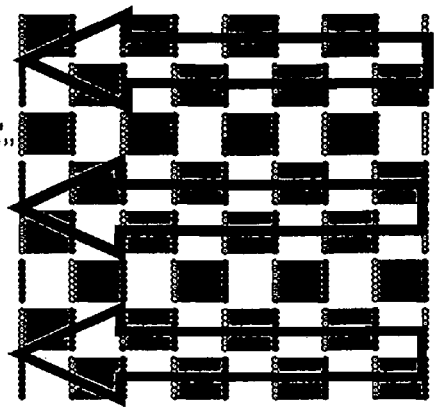
FIG. 8a-f fluid flows, respectively electrophoretic particle flows on the entire chip, respectively from selected segments of the chip.
Figure 8B:
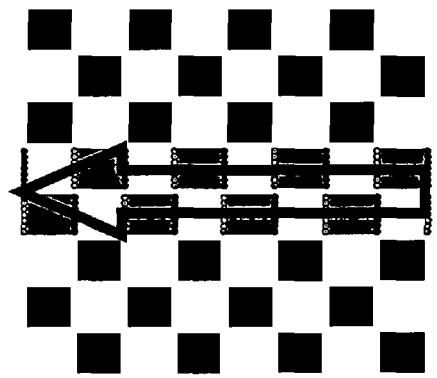
Figure 8C:
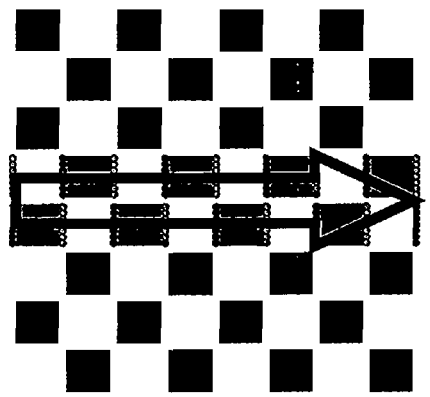
Figure 8D:
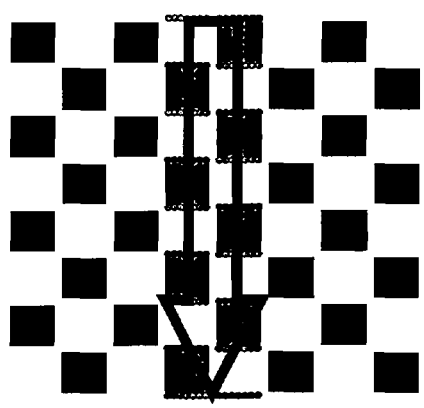
Figure 8E:
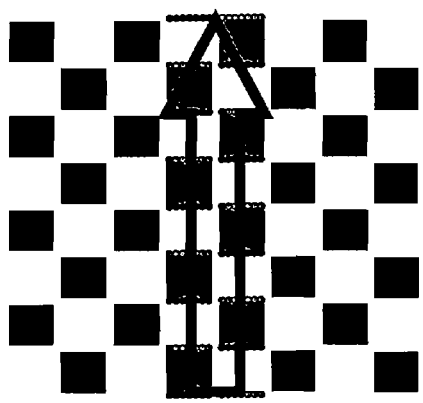
Figure 8F:
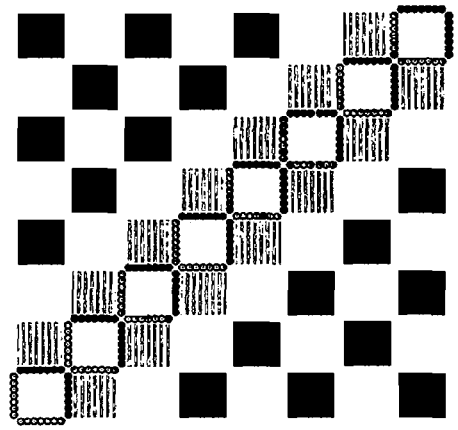

The basic functions, fluid transport and/or electrophoretic particle transport, are illustrated in FIG. 8a through 8f:

FIG. 8a shows the applied voltages which generate a fluid flow, respectively an electrophoretic particle flow in the east-west direction on the entire chip segment;

FIG. 8b shows the applied voltages which generate a fluid flow, respectively an electrophoretic particle flow in the east-west direction on one strip of the chip segment;

FIG. 8c shows the applied voltages which generate a fluid flow, respectively an electrophoretic particle flow in the west-east direction on one strip of the chip segment;

FIG. 8d shows the applied voltages which generate a fluid flow, respectively an electrophoretic particle flow in the north-south direction on one strip of the chip segment;

FIG. 8e shows the applied voltages which generate a fluid flow, respectively an electrophoretic particle flow in the south-north direction on one strip of the chip segment;

FIG. 8f shows the applied voltages which generate a fluid flow, respectively an electrophoretic particle flow in the diagonal direction from southwest to northeast on one strip of the chip segment.

Figure 9A:
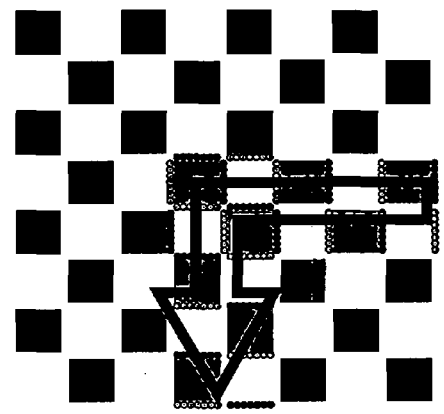
FIG. 9a-c bifurcations in the fluid flows, respectively electrophoretic particle flows on the chip.
Figure 9B:
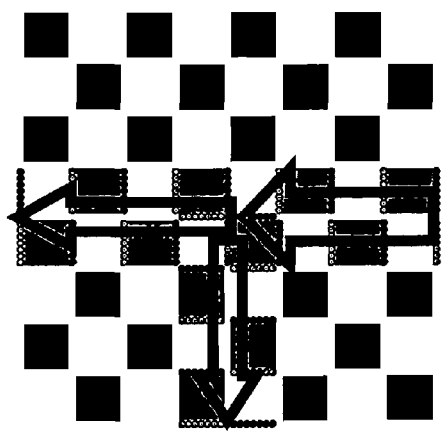
Figure 9C:
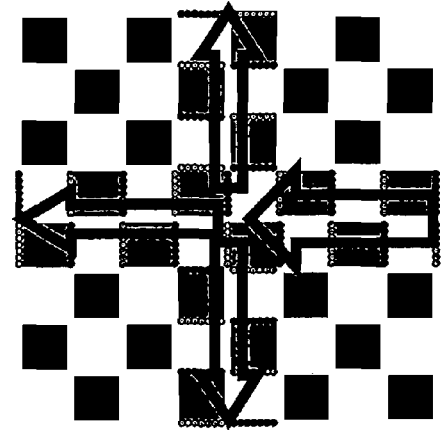

The basic functions, flow bifurcation and flow branching and/or bifurcations and branchings of an electrophoretic particle flow, are illustrated in FIG. 9a through 9c:

FIG. 9a shows the applied voltages for a fluid flow, respectively an electrophoretic particle flow. A partial flow emanating from the east-west direction is deflected into the north-south direction.

FIG. 9b shows the applied voltages for a fluid flow, respectively an electrophoretic particle flow. A partial flow emanating from the east-west direction bifurcates into the north-south direction.

FIG. 9c shows the applied voltages for a fluid flow, respectively an electrophoretic particle flow. A partial flow emanating from the east-west direction bifurcates into the north-south direction and into the south-north direction, respectively.

Figure 10A:
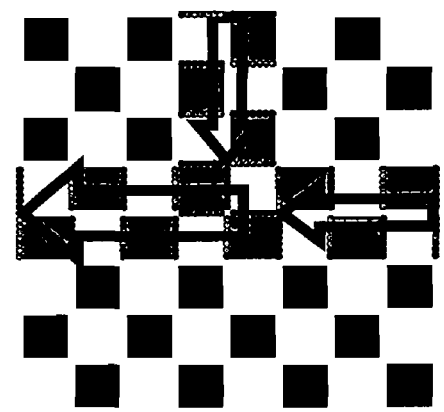
FIG. 10a-b fluid flows, respectively electrophoretic particle flows on the chip, including confluence sites.
Figure 10B:
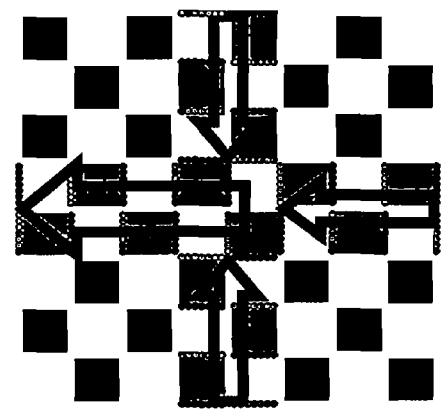

The basic functions, flow inflow and/or inflow of the electrophoretic particle flow, are illustrated in FIGS. 10a and 10b:

FIG. 10a shows the applied voltages for a fluid flow, respectively an electrophoretic particle flow in the east-west direction. A partial flow emanating from the north-south direction flows in.

FIG. 10b shows the applied voltages for a fluid flow, respectively an electrophoretic particle flow in the east-west direction. A partial flow emanating from the north-south direction and from the south-north direction, respectively, flows in.

The basic function, flow intersection and/or intersection of electrophoretic particle flows, is clarified using a traffic light as an example. FIG. 11a through 11d show, as a time sequence, how two flows and/or particle flows intersect without mixing in the process. If there are special requirements for the purity of the flows, respectively of the flows, the intersection region is additionally rinsed.

It is illustrated how a first fluidic flow, respectively particle flow, is halted by the intersection and a second fluidic flow, respectively particle flow, perpendicular thereto is conducted through the same intersection.

Figure 11A:
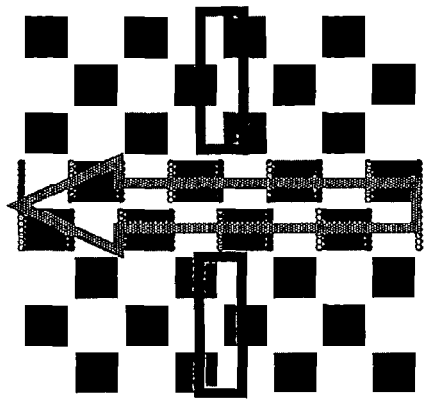
FIG. 11a-d intersection of fluid flows, respectively electrophoretic particle flows on the chip.
Figure 11B:
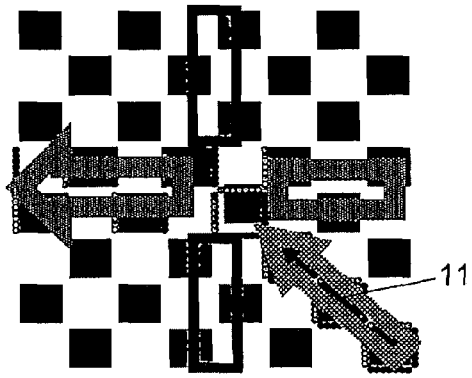

FIG. 11a shows a flow/a particle flow in the east-west direction;

FIG. 11b shows how the flow, respectively the particle flow is halted in the east-west direction. The intersection region is subsequently filled with a rinsing liquid 11.

Figure 11C:
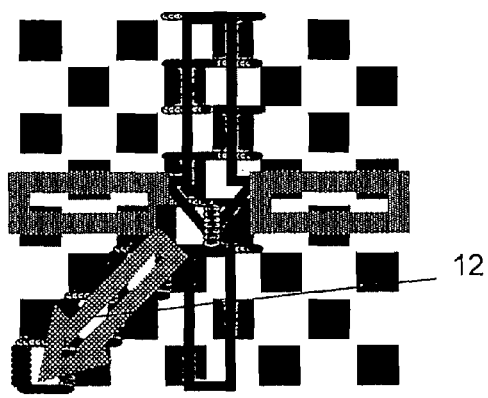

FIG. 11c illustrates how the interruption of the fluidic flow, respectively the particle flow, in the north-south direction is closed by draining a drainage fluid 12.

Figure 11D:
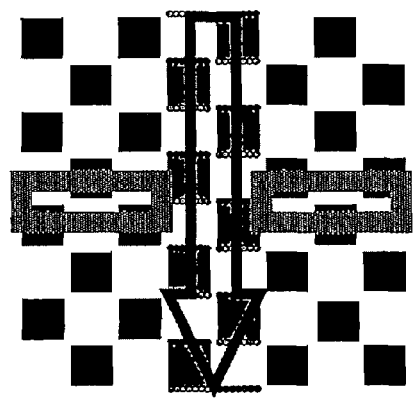

FIG. 11d shows a flow/a particle flow in the north-south direction. The process described in FIG. 11a through 11d may be continued in such a way that the flow, respectively the particle flow, flows alternately in the east-west and north-south direction. This kind of periodic repetition results in two flows, respectively particle flows, continuously intersecting without mixing thereof.

The basic functions, flow mixer, respectively mixing of at least partially electrically charged particles, are clarified with reference to the examples from FIG. 12a through 15. In one embodiment according to the present invention, flows are able to be mixed in a lamination process. In an alternating process, the fluids to be mixed are fed orthogonally to a cross flow, so that a mixing by diffusion takes place in the cross flow direction.

Figure 12A:
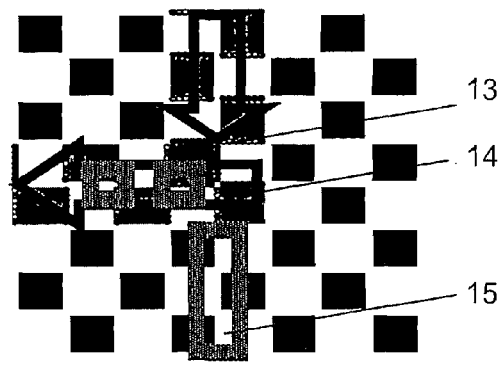
FIG. 12a-b flow mixing or metering/tagging based on lamination.

FIG. 12a shows the flow of medium 13 in the north-south direction and cross flow 14 in the east-west direction; medium 15 is at equilibrium.

Figure 12B:
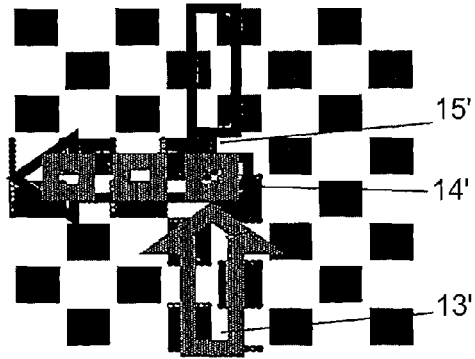

FIG. 12b shows the flow of medium 13' in the south-north direction and cross flow 14' in the east-west direction; medium 15' is at equilibrium. This process may be repeated multiple times. Analogously, particle flows of at least partially electrically charged particles may be arranged in a laminated configuration in a cross flow having alternating layers, and be mixed, respectively transported. Analogously, a first particle type may also be metered into a second particle type, or the site in a fluid or the fluid itself may be tagged.

Figure 13:
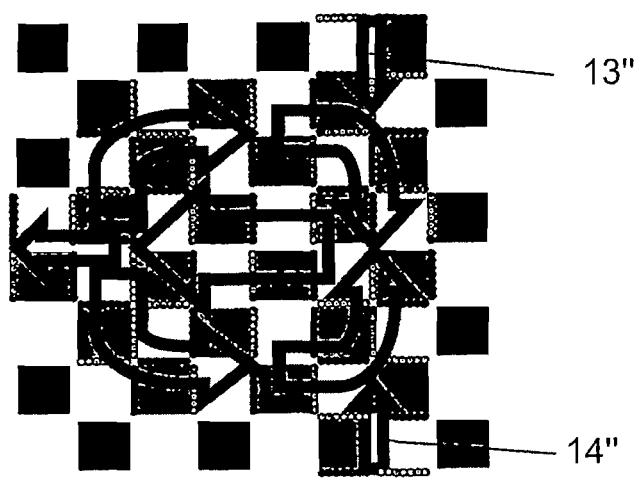
FIG. 13 flow mixing based on back-mixing.

In another embodiment, flows in accordance with FIG. 13 are mixed by back-mixing. Flows 13", 14" first converge in a confluence. A substantial portion of the flow is removed in a bifurcation, and fed in again upflow in a confluence. An analogous method may be used to mix particle flows of at least partially electrically charged particles.

Figure 14:
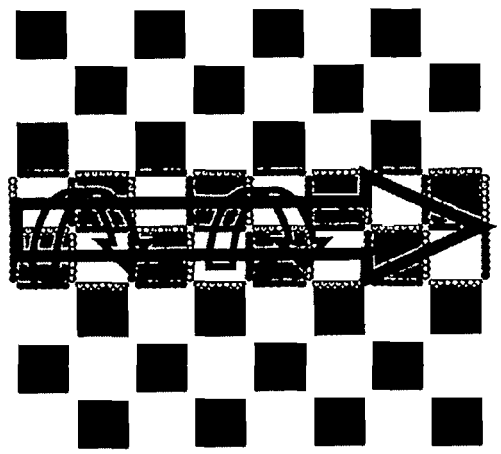
FIG. 14 flow mixing based on secondary flow.

In another embodiment, flows in accordance with FIG. 14 are mixed by secondary flows in the vertical direction. Here, the principal flow runs in the west-east direction. At the wall, a superposed flow is produced in the south-north direction, which may only be completed in wall-remote layers by a wall-normal flow and a flow in the opposite direction.

Figure 15:
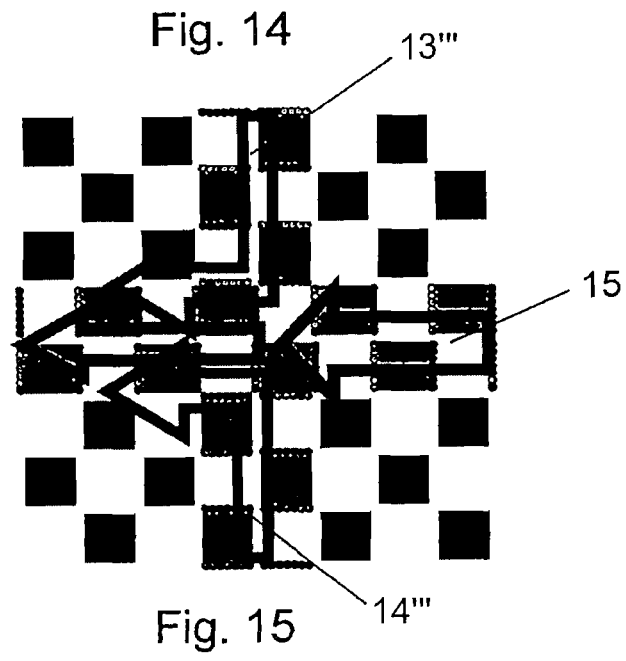
FIG. 15 focusing of a medium/species by lateral feeding of two fluid flows.

In another embodiment, particle flows are focused in flows in accordance with FIG. 15. To that end, a particle flow 15 is fed in the east-west direction. Flows 13''', 14''' are fed from the north direction and the south direction to the particle flow, thereby focusing the same.

FIG. 16a-e show a complete application including individual basic functions for analyzing an ion mixture. To that end, the embodiment in accordance with FIG. 7 is used. Reservoirs 21, 22, 23, 25 are added to the structure according to FIG. 7. In addition, a conductivity detector 24 is integrated into the structure. The structure and the reservoirs 22, 23, 25 are filled with a buffer. Reservoir 21 is filled with an ion mixture whose composition is to be analyzed. All of the processes described in the following are realized in that they are controlled by electric fields in the base and in the cover of the lab on a chip.

Figure 16A:
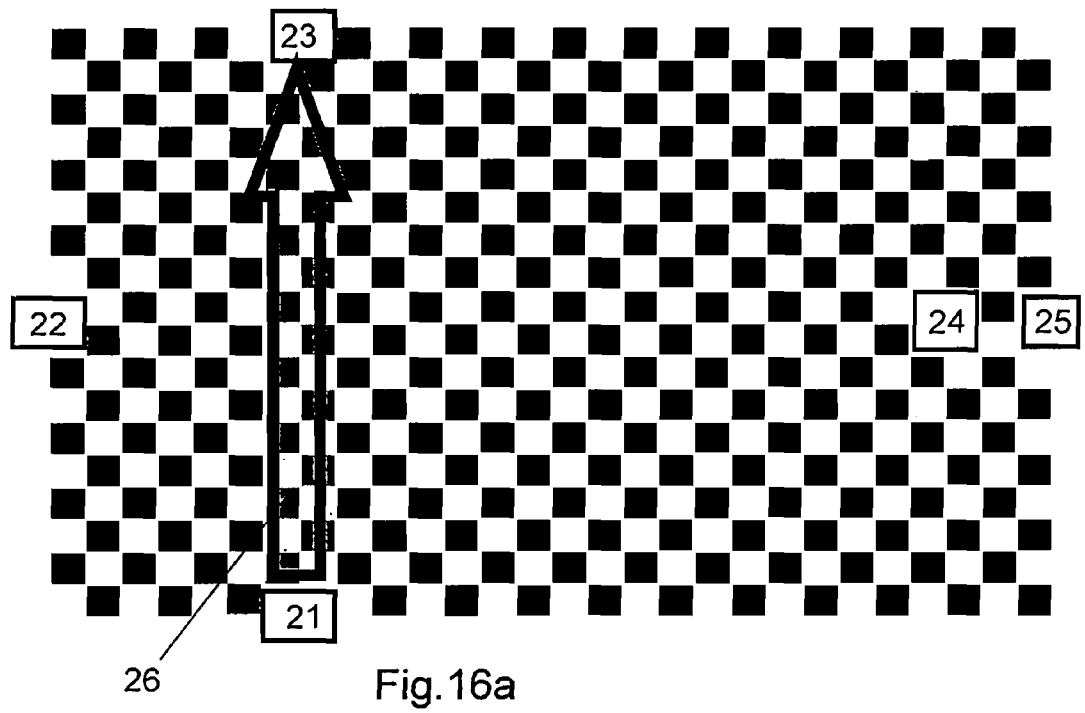
FIG. 16a-e design layout of a lab on a chip for ion analysis.

FIG. 16a shows the transporting of the ion mixture from reservoir 21 in the direction of reservoir 23. To that end, a flow, respectively a particle flow 26 is implemented in accordance with FIGS. 2a and c. It is advantageous that the ion mixture is transported on the lab on a chip without electrophoretic separation.

Figure 16B:
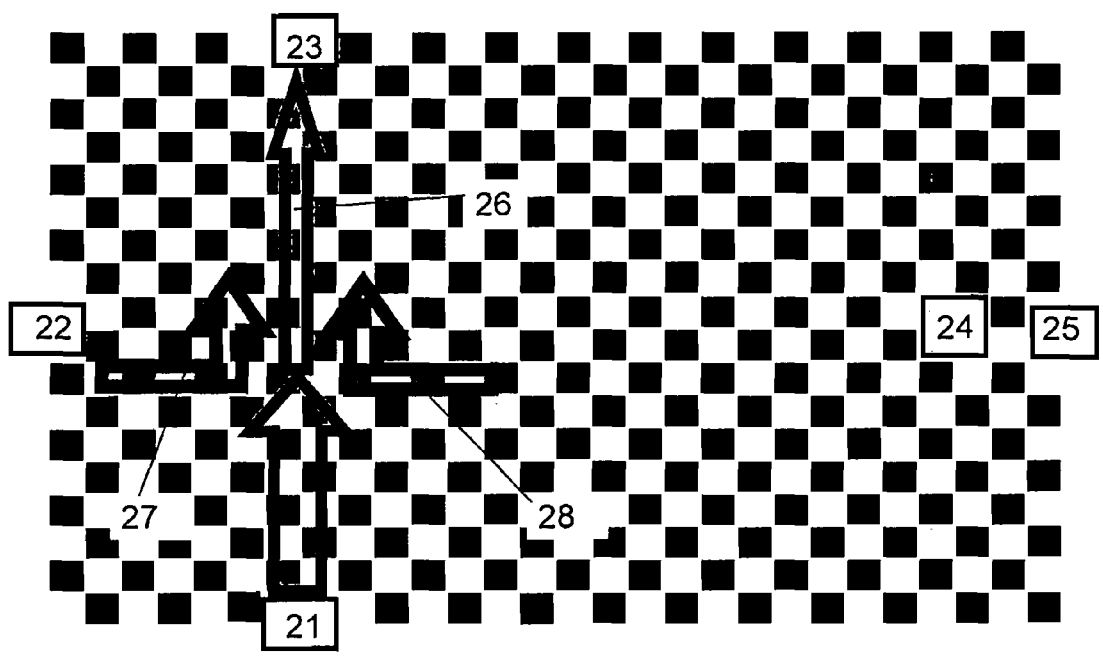

FIG. 16b shows the focusing of the particle flow since this initial condition has a positive effect on the separation efficiency of an electrophoretic process. If the ion mixture reaches the middle of the lab on a chip, a focusing follows in accordance with FIG. 15. To that end, two lateral fluid flows 27, 28 are produced which constrict the flow, respectively particle flow 26.

Figure 16C:
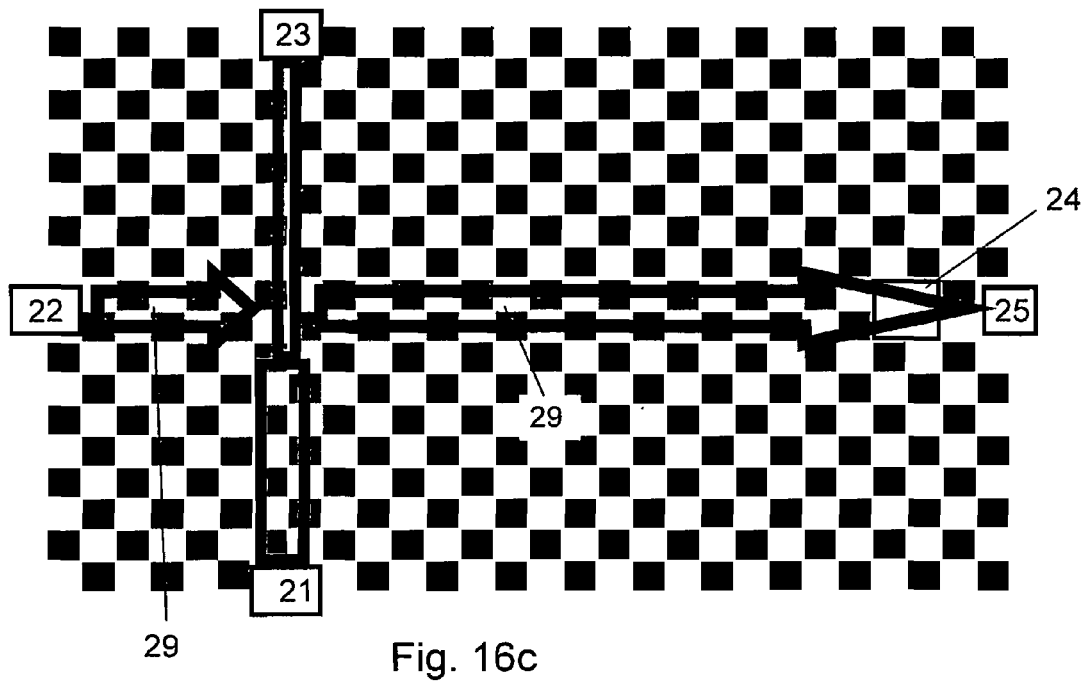

FIG. 16c shows the beginning of the separation process. To that end, in the middle of the lab on a chip, a flow 29 flows from reservoir 22 to reservoir 25 in accordance with FIGS. 2a and c. A small plug is thereby extracted from the focused particle flow and fed in the direction of reservoir 25, respectively of conductivity detector 24.

Figure 16D:
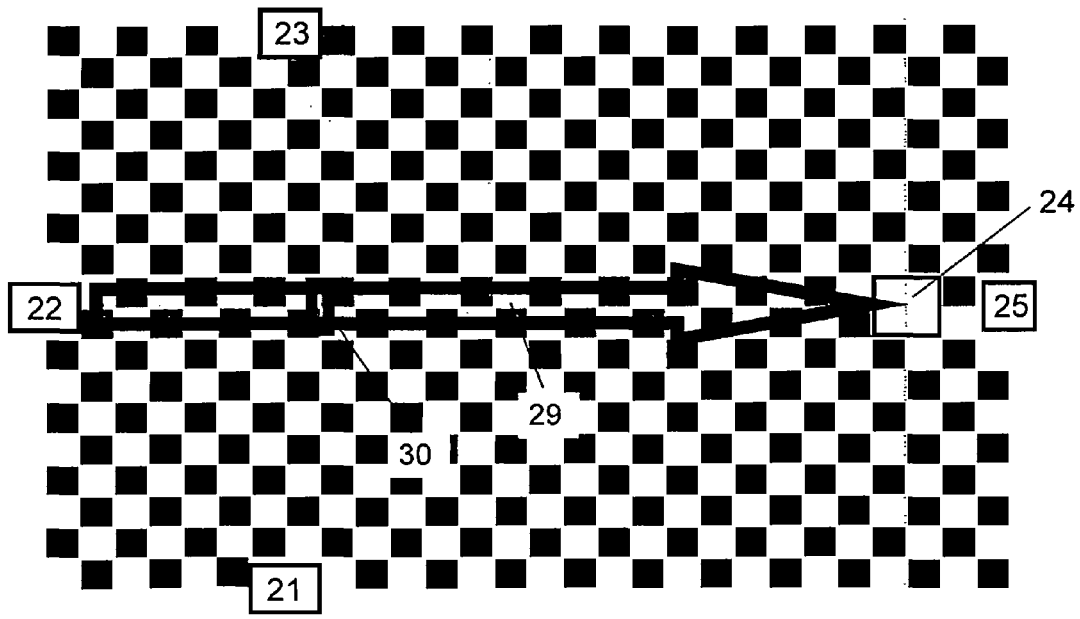

FIG. 16d shows the separation process. To that end, the electrodes are interconnected between reservoir 22 and reservoir 25 in accordance with FIGS. 6a and b. Thus, plug 30 of the ion mixture passes only through rectified electric fields.

Figure 16E:
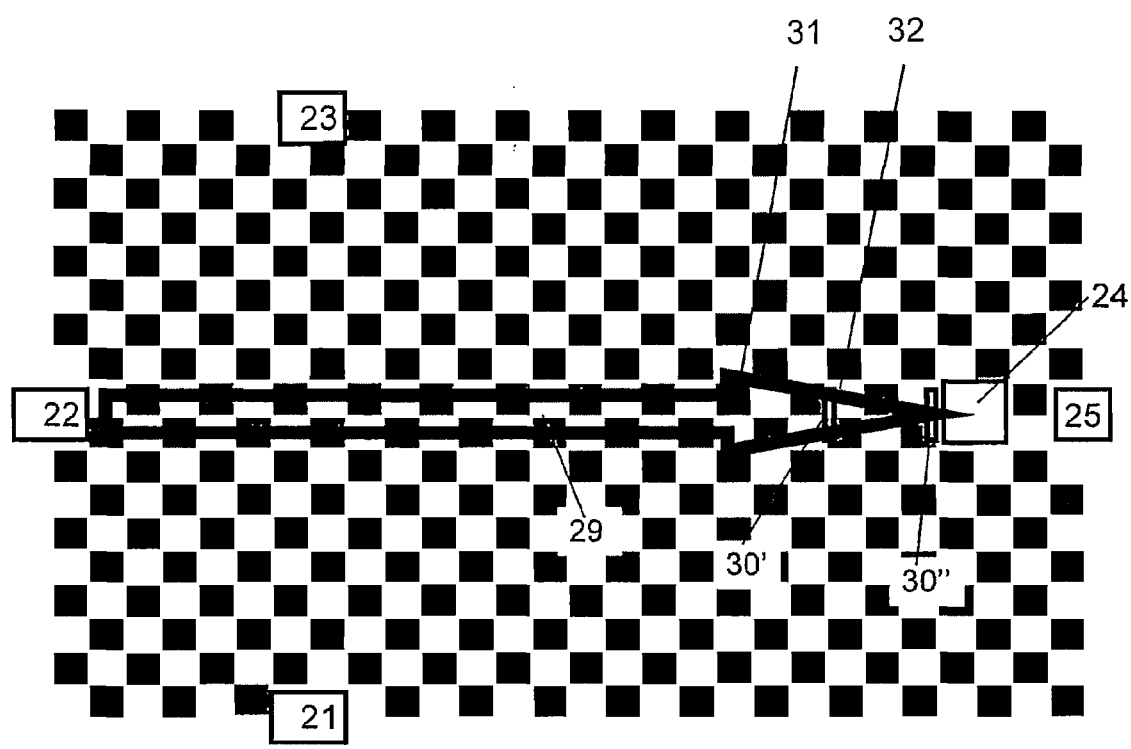

The result is a situation as illustrated in FIG. 16e. On the basis of the specific mobilities, plug 30' separates into its constituents 31 and 32. The constituents reach conductivity detector 24 at different points in time. Therefore, the time required therefore is characteristic of the component, while the ascertained conductivity is proportional to the concentration of the constituents

The invention claimed is:

1. A device for producing at least one of fluid flows and particles flows, the device comprising:
   a substrate having a substrate surface, the substrate surface including a matrix having a plurality of regions in a two dimensional array, so that the plurality of regions are arranged in a checkered pattern with adjacent regions of the plurality of regions having at least one of a different magnitude of a surface charge, a different sign of the surface charge, and a different height above the substrate;

a fluid disposed at the substrate surface, the fluid including at least partially electrically charged particles;

a plurality of electrode pairs disposed on the substrate surface; and a first control element configured to supply a plurality of electrical voltages to the plurality of electrode pairs so as to generate, by each of the plurality of electrode pairs, an electric field in response thereto, wherein the electric field exerts a first force on a component of the fluid within an electrical double layer, the component being disposed adjacent to the substrate surface, and wherein the electric field exerts a second force within the double layer and outside of the double layer, the second force being exerted on the at least partially electrically charged particles.

2. The device as recited in claim 1, wherein the plurality of electrode pairs include a respective electrode pair disposed between each of the adjacent regions of the plurality of regions.

3. The device as recited in claim 1, wherein the substrate surface includes a semiconductor material, a surface charge of the semiconductor material in each of the plurality of regions being adjustable individually or in groups using the first control element or using a second control element.

4. The device as recited in claim 1, wherein adjacent regions of the plurality of regions include different materials.

5. The device as recited in claim 4, wherein a first region of the regions includes a glass and a second region of the regions includes a metal oxide having a positive surface charge, the first and second regions being adjacent to each other.

6. The device as recited in claim 4, wherein a first region of the regions includes a polymer having a first surface charge and a second region of the regions includes a polymer having a second surface charge different from the first surface charge, the first and second regions being adjacent to each other.

7. The device as recited in claim 1, wherein adjacent regions have similar dimensions.

8. The device as recited in claim 1, wherein the device is configured as at least one of a programmable microfluidic analysis unit and a synthesis unit.

9. The device as recited in claim 1, wherein the device is configured so as to cool an adjacent microelectronic component or processor.

10. The device as recited in claim 1, further comprising:
an auxiliary substrate having an auxiliary substrate surface, the auxiliary substrate surface including a plurality of auxiliary regions having at least one of a different magnitude of an auxiliary surface charge, a different sign of the auxiliary surface charge, and a different auxiliary height above the auxiliary substrate surface;

a plurality of auxiliary electrode pairs disposed on the auxiliary substrate surface; and a first auxiliary control element configured to supply a plurality of auxiliary electrical voltages to the plurality of auxiliary electrode pairs, wherein each of the plurality of auxiliary electrode pairs is configured to generate, by each of the plurality of auxiliary electrode pairs, an auxiliary electric field in response thereto, wherein the auxiliary electric field exerts a first auxiliary force on an auxiliary component of the fluid disposed adjacent to the auxiliary substrate surface within an auxiliary electrical double layer, wherein the auxiliary electric field exerts a second auxiliary force within the auxiliary double layer and outside of the auxiliary double layer, the second auxiliary force being exerted on the at least partially electrically charged particles, and wherein the fluid is disposed between the substrate and the auxiliary substrate.

11. A method for making a device for producing at least one of fluid flows and particles flows, the method comprising:
providing a substrate having a substrate surface;
providing a plurality of electrode pairs on the substrate surface;
providing a fluid at the substrate surface, the fluid including at least partially electrically charged particles;
providing a first control element configured to interconnect the plurality of electrode pairs; and
treating the substrate surface so as to subdivide the substrate surface in a matrix having a plurality of regions in a two-dimensional array, so that the plurality of regions are arranged in a checkered pattern with adjacent regions of the plurality of regions having at least one of:
a different magnitude of a surface charge,
a different sign of the surface charge, and
a different height above the substrate.

12. The method as recited in claim 11, wherein the plurality of electrodes are disposed on the substrate surface so as to subdivide the substrate surface into the matrix of regions with a respective electrode disposed between each of the adjacent regions of the matrix of regions.

13. The method as recited in claim 11, wherein a first region of a pair of the adjacent regions includes at least one coating having a surface charge with a different magnitude or sign from a surface charge of the substrate surface.

14. The method as recited in claim 11, wherein the substrate surface includes a semiconductor material having a substrate surface charge disposed in at least one of the plurality of regions, the substrate surface charge adjustable using the first control element or a second control element.

15. The method as recited in claim 11, wherein a first region of a pair of the adjacent regions includes a recess.

16. The method as recited in claim 11, wherein the first control element is configured to provide at least two of the plurality of electrode pairs with a respective positive and negative potential difference so as to at least one of flow the fluid and move the particles.

17. The method as recited in claim 16, wherein the plurality of electrode pairs are configured to be controlled individually or in groups of at least two electrode pairs.

18. The method as recited in claim 11, wherein the device is configured as at least one of a programmable micro fluidic analysis unit and a synthesis unit.

19. The method as recited in claim 11, wherein the device is configured to cool an adjacent microelectronic component or processor.

* * * * *